US006093699A

United States Patent [19]
Sehon et al.

[11] Patent Number: 6,093,699

[45] Date of Patent: Jul. 25, 2000

[54] METHOD FOR GENE THERAPY INVOLVING SUPPRESSION OF AN IMMUNE RESPONSE

[75] Inventors: Alec Sehon, Winnipeg, Canada; Judith A. Kapp, Atlanta, Ga.; Glen M. Lang, Winnipeg, Canada; Yong Ke, Carmel, Ind.

[73] Assignees: The University of Manitoba, Manitoba, Canada; Emory University, Atlanta, Ga.

[21] Appl. No.: 08/339,245

[22] Filed: Nov. 10, 1994

Related U.S. Application Data

[63] Continuation-in-part of application No. 07/877,368, May 4, 1992, Pat. No. 5,447,722, which is a continuation of application No. 07/707,972, May 23, 1991, abandoned, which is a continuation of application No. 07/478,049, Feb. 7, 1990, abandoned, which is a continuation of application No. 07/071,462, Jul. 9, 1987, abandoned.

[51] Int. Cl.[7] .......................... A01N 43/04; A61K 31/70; C12N 15/00; C12N 15/63

[52] U.S. Cl. ......................... 514/44; 435/320.1; 435/455; 424/93.21; 424/178.1; 424/193.1; 424/280.1; 424/810; 424/85; 530/389; 530/391

[58] Field of Search ........................... 514/44; 424/178.1, 424/193.1, 280.1, 810, 85, 93.21; 530/389, 391; 435/320.1, 455

[56] References Cited

U.S. PATENT DOCUMENTS

| | | | |
|---|---|---|---|
| 4,261,973 | 4/1981 | Lee et al. | 424/78.3 |
| 4,276,206 | 6/1981 | Katz | 525/54.1 |
| 4,296,097 | 10/1981 | Lee et al. | 424/78.28 |
| 4,430,260 | 2/1984 | Lee et al. | 525/61 |
| 4,650,675 | 3/1987 | Borel | 424/85 |
| 5,358,710 | 10/1994 | Sehon | 424/178.1 |
| 5,399,346 | 3/1995 | Anderson | 424/93.21 |

OTHER PUBLICATIONS

Sehon, A.H., "Cytokine Gene Expression of CD8+ Suppressor T Cells Induced by Tolerogenic Conjugates of Antigen and mPEG" (1993) Cellular Immunology, 149: pp. 409–421.

Sehon, A.H., "Conversion of Antigens to Tolerogenic Derivatives by Conjugation w/mPEG" (1987) Molecular Cell Biology, 65:pp. 205–219.

Marshall, Eliot, "Gene Therapy's Growing Pains" (1995), Science, 269: pp. 1050–1054.

"Report and Recommendations of the Panel to Assess the NIH Investment in Research on Gene Therapy" (1995).

Sehon, S.H., "Down Regulation of IgE Antibodies by Suppressogenic Conjugates" (1983) Academi Press Japan, Inc. pp. 483–491.

Sehon, A.H., "Modulation of Antibody Responses by Conjugates of Antigens with Monomethoxypolyethylene Glycol", from Immunobiology of Proteins and Peptides V, Plenum Publishing Corp., (1989).

Sehon, A.H., "Immunological Strategies for Therapeutic Destruction and HIB–Infected Cells in Asymptomatic Patients", MCR Group for Allergy Research, pp. 570–574.

Sehon, A.H., Potential use of Allergens Modified with Monomethoxypolyethylene Glycol for Immunotherapy of Atopic Patients, pp. 313–318.

Handbook of Experimental Immunology, 2nd edition, Ed. S.M. Weir, Blackwell Scientific Publication, Oxford 1973, p. 35.3.

Bitoh et al. (1993) Cellular Immunol 150: (68–93.

Culver M.D., Kenneth W., "Gene Therapy", A Handbook for Physicians.

*Primary Examiner*—Deborah Crouch
*Assistant Examiner*—Jill D. Martin
*Attorney, Agent, or Firm*—Antonelli, Terry, Stout & Kraus, LLP

[57] ABSTRACT

A method for specifically suppressing the capacity of a mammal receiving gene therapy to mount an immune response to a given expressed gene of the deficient gene in question, which response is caused by the administration of "foreign" DNA encoding an antigenic protein or vectors comprising such DNA for expression of the deficient gene in the patient receiving gene therapy.

3 Claims, 2 Drawing Sheets

METHOD FOR GENE THERAPY INVOLVING SUPPRESSION OF AN IMMUNE RESPONSE

This application is a continuation-in-part of pending U.S. application Ser. No. 07/877,368, filed on May 4, 1992 by Lang et al., now U.S. Pat. No. 5,447,722, which is a continuation of abandoned U.S. application Ser. No. 07/707, 972, filed on May 23, 1991 by Lang et al., which is a continuation of abandoned U.S. application Ser. No. 07/478, 049, filed on Feb. 7, 1990 by Lang et al., which is a continuation to abandoned U.S. application Ser. No. 07/071, 462, filed on Jul 9, 1987 by Lang et al.

FIELD OF THE INVENTION

The present invention relates to a method for suppressing the capacity of a mammal to mount an immune response caused by the administration of one or more immunogenic therapeutic material(s), such as gene vectors or their expression proteins used in applications to gene therapy.

BACKGROUND

Foreign proteins or DNA, such as genetic material or vectors for gene therapy, or their derivatives, have therapeutic properties and are administered to patients suffering from certain diseases. However, as discussed later, the immunogenicity of the said foreign proteins, nucleotides, DNA or vectors, or of their derivatives, may vitiate the treatment and hence this invention provides an improved method for the treatment of such diseases.

Gene therapy is the insertion of a functioning gene into the cells of a patient (i) to correct an inborn error of metabolism (i.e., genetic abnormality or birth defect resulting in the deficiency of the patient with respect to one or more essential proteins such as enzymes or hormones), or (ii) to provide a new function in a cell (Kulver, K. W., "Gene Therapy", 1994, p. xii, Mary Ann Liebert, Inc., Publishers, New York, N.Y.).

When the host is totally deficient of the inserted gene from birth, the new protein expressed by this gene—when the latter is inserted into the appropriate cell of an adult host—would be expected to induce in the host an immune response against itself. Hence, (i) the host would produce antibodies or cytotoxic cells to the "new" protein, and (ii) this immune response would not only combine and neutralize and thus inactivate the function of the "new" protein, but may also lead to untoward therapeutic complications due to formation of immune complexes. It is, therefore, not surprising that gene therapy has proven successful in adenosine deaminase (ADA) deficiency, i.e., in children deficient of ADA from birth, which is manifested by the absence of functional T lymphocytes and consequently to the severe combined immunodeficiency (SCID) syndrome. The reported success of gene therapy in young children deficient of ADA from birth is related to the immunodeficient status of the child, as no immune response can be generated against the foreign therapeutic genetic material. As a corollary, gene therapy would be successful it it is instituted from birth, when it is relatively easy to induce immunological tolerance to a foreign immunogenic material.

Foreign immunogenic materials, such as biologic response modifiers or their derivatives, often have therapeutic properties and are, therefore, administered to patients suffering from certain diseases. However, as a result of the immunogenicity of the foreign materials, or of their derivatives, for the reasons stated above the insertion of the appropriate gene may vitiate the desired therapeutic effects. This invention provides a method for overcoming this inherent complication due to the immunogenic capacity of the expressed protein, and is therefore considered to represent a novel and an essential improvement for the treatment of such diseases.

As Background to the present invention:

Chen, Y., Takata, M., Maiti, P. K., Mohapatra, S., Mohapatra, S. S. and Sehon, A. H., disclose that the suppressor factor of Ts cells induced by tolerogenic conjugates of OVA and mPEG is serologically and physicochemically related to the $\alpha\beta$ heterodimer of the TCR. *J. Immunol.* 152:3–11, 1994.

Mohapatra, S., Chen, Y., Takata, M., Mohapatra, S. S. and Sehon, A. H. disclose "Analysis of TCR $\alpha\beta$ chains of $CD8^+$ suppressor T cells induced by tolerogenic conjugates of antigen and monomethoxypolyethylene glycol: Involvement of TCR $\alpha$-CDR3 domain in immuno-suppression." *J. Immunol.* 151:668–698, 1993.

Bitoh, S., Takata, M., Maiti, P. K., Holford-Stevens, V., Kierek-Jaszczuk, D. and Sehon, A. H., disclose that "Antigen-specific suppressor factors of noncytotoxic $CD8^+$ suppressor T cells downregulate antibody responses also to unrelated antigens when the latter are presented as covalently linked adducts with the specific antigen." *Cell. Immunol.* 150:168–193, 1993.

Bitoh, S., Lang, G. M., Kierek-Jaszczuk, D., Fujimoto, S. and Sehon, A. H., disclose "Specific immunosuppression of human anti-murine antibody (HAMA) responses in hu-PBL-SCID mice." *Hum. Antibod. Hybridomas* 4:144–151, 1993.

Bitoh, S., Lang, G. M. and Sehon, A. H., disclose the "Suppression of human anti-mouse idiotypic antibody responses in hu-PBL-SCID mice." *Hum. Antibod. Hybridomas* 4:144–151, 1993.

Dreborg, S. and Akerblom, E., disclose the safety in humans of "Immunotherapy with monomethoxypolyethylene glycol modified allergens." In: S. D. Bruck (Ed.), *CRC Crit. Rev. Ther. Drug Carrier Syst.* 6:315–363, (1990).

Generally the term antigen refers to a substance capable of eliciting an immune response and ordinarily this is also the substance used for detection of the corresponding antibodies by one of the many in vitro and in vivo immunological procedures available for the demonstration of antigen-antibody interactions.

Similarly, the term allergen is used to denote an antigen having the capacity to induce and combine with reaginic (i.e., IgE) antibodies which are responsible for common allergies; however, this latter definition does not exclude the possibility that allergens may also induce reaginic antibodies, which may include immunoglobulins of classes other than IgE.

As used herein, the term antigenicity is defined as the ability of an antigen (immunogenic material) or allergen to combine in vivo and in vitro with the corresponding antibodies; the term allergenicity or skin activity is defined as the ability of an allergen to combine in vivo with homologous reaginic antibodies thereby triggering systemic anaphylaxis or local skin reactions, the latter reactions being the result of direct skin tests or of passive cutaneous anaphylactic (PCA) reactions; and the term immunogenicity in a general sense is the capacity of an antigen or allergen, or of their derivatives produced in vitro or processed in vivo, to induce the corresponding specific antibody response.

In relation to this invention, tolerogens are defined as immunosuppressive covalent conjugates consisting of an antigenic material (immunogenic proteins, etc.) and a water-soluble polymer (see e.g. Sehon, A. H., In "Progress in Allergy" (K. Ishizaka, ed.) Vol. 32 (1982) pp. 161–202, Karger, Basel; and U.S. Pat. No. 4,261,973).

In the present context and claims the term tolerogen thus refers to a conjugate consisting of an immunogenic material (protein or polynucleotide) and a nonimmunogenic conjugate, said tolerogen being immunosuppressive in an immunologically specific manner with respect to the antigen which is incorporated into the tolerogenic conjugate irrespective of the immunoglobulin class which is downregulated; furthermore, the tolerogen may comprise a conjugate of an essentially nonimmunogenic polymer and an immunogenic biologically active product or derivative of the genetic material used for gene therapy.

The therapeutic administration of foreign immunogenic material induces an immune response leading to the formation of antibodies of different immunoglobulin classes. Hence, on repeated administration, the material may form complexes in vivo with such antibodies leading to a poor therapeutic effect by virtue of its being sequestered and neutralized by the antibodies, or to anaphylactic reactions by combination with reaginic antibodies, or to other untoward conditions, i.e. immune complex diseases due to the deposition of antibody-antigen complexes in vital tissues and organs.

Wilkinson et al. "Tolerogenic polyethylene glycol derivatives of xenogenic monoclonal immunoglobulins", *Immunoloqy Letters*, Vol. 15 (1987) pp. 17–22, discloses the criticality of the administration time of a tolerogenic conjugate to a non-sensitized individual at least one day prior to challenge with an antigen.

The present invention overcomes deficiencies of the prior art, providing a means for inducing a priori tolerance to a protein or polynucleotide in an individual deficient of the given protein or polynucleotide, thus making the administration of gene therapy—which involves the generation of immunogenic material in a patient deficient of the corresponding gene—possible and effective.

SUMMARY OF THE INVENTION

Gene therapy procedures as currently practiced—involve the administration by itself of a foreign genetic material, or of its biologically active products—do have certain disadvantages and limitations which are primarily due to their potential immunogenicity in the host deficient of the corresponding gene. The objectives of the present invention aim at overcoming the above mentioned complications by suppressing the production of antibodies to the foreign therapeutic genetic material and of its expression products, and of thus ensuring the efficacy of gene therapy by the prior administration of immunosuppressive doses of tolerogenic conjugates consisting of therapeutically active and potentially immunogenic materials coupled to nonimmunogenic polymers, thus overcoming or minimizing the risk of inducing anaphylactic reactions or immune complex diseases. Thus, the main objective of the invention aims at suppressing substantially an immune response to the protein resulting as a consequence of successful gene therapy, which response would undermine the therapeutic efficacy of a biologically active genetic material and which may also cause untoward physiological reactions (e.g. anaphylaxis and/or immune complex diseases).

The invention provides a method for conducting gene therapy comprising administration to a mammal of an immunosuppressing effective amount of a tolerogenic conjugate comprising the genetic material and/or its expression product (i.e., the protein of which the patient is deficient) and monomethoxypolyethylene glycol having a molecular weight of about 4,500–10,000 daltons, the above administration being at least one day prior to administration of the therapeutic genetic material for gene therapy, wherein said method results in the specific suppression of the immune response and the active development of specific tolerance to said therapeutic genetic material and/or its expression product(s).

In a preferred embodiment the therapeutic genetic material is selected from nucleotides, DNA, RNA, MRNA, attached to appropriate vectors for expression of the required therapeutic protein.

In a more preferred embodiment gene therapy vectors include Moloney murine leukemia virus vectors, adenovirus vectors with tissue specific promoters, herpes simplex vectors, vaccinia vectors, artificial chromosomes, receptor mediated gene delivery vectors, and mixtures of the above vectors.

DESCRIPTION OF THE INVENTION

Figure 1:
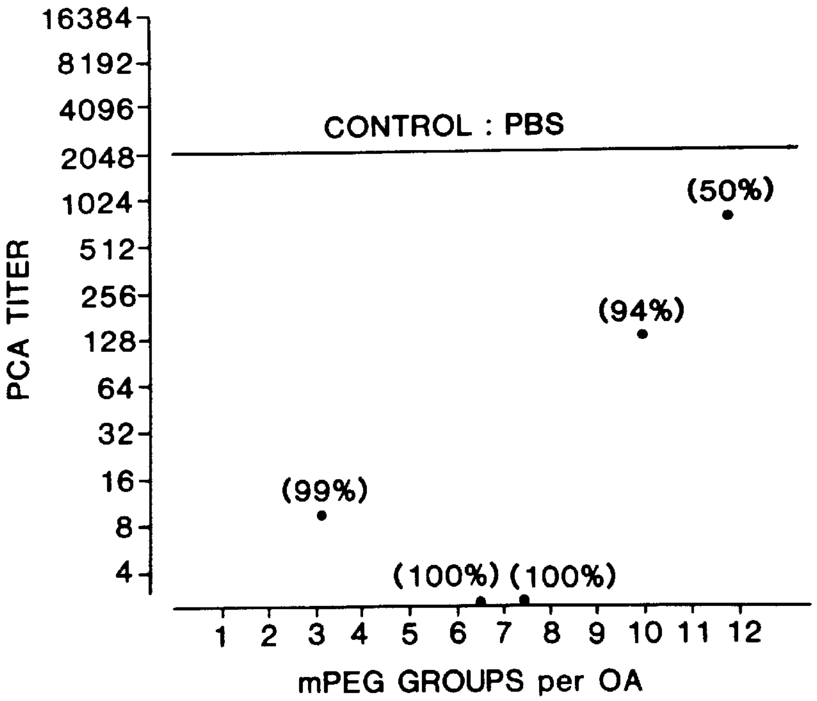
FIG. 1 is a diagram illustrating the suppressogenic relationship between treatment of (B6D2)F1 mice with OA-mPEG conjugates of different molecular compositions and the primary anti-OA IgG response, as measured by PCA titers. The percentages in brackets represent the degree of suppression with respect to the minimal immune response in animals receiving phosphate buffered saline (PBS) in lieu of the conjugates.

The objectives of the present discovery are accomplished by a method, wherein an immunosuppressively effective amount of a tolerogen incorporating a foreign genetic material or its active derivative(s) is administered to the mammal prior to the administration of the foreign genetic material or its biologically active derivative(s). The tolerogenic conjugate is preferably administered to individuals who have not received a prior treatment with the foreign genetic material or its product, i.e. to unsensitized individuals.

The invention will provide improved methods for gene therapy of different human diseases which can be ameliorated or eliminated by the administration of the appropriate genetic materials, etc. or their therapeutic derivatives, of which the patient is deficient. The tolerogenic conjugates may be synthesized by covalent or noncovalent attachment of nonimmunogenic polymers to natural or synthetic biologically active proteins such as for example (i) murine or rat monoclonal antibodies to human T-cells which have been used to suppress transplant rejection (Colvin, R. B. et al.;

Fed. Proc. 41 (1982) p. 363, Abstr. 554) or as "miracle bullets" for the destruction of tumors (Froese, G. et al.; Immunology 45 (1982) p. 303–12, and Immunological Reviews 62 (1982), Ed. G. Möller, Munksgaard, Copenhagen), (ii) enzymes, such as superoxide dismutase (Kelly, K. et al.; Cdn. J. of Physiol. Pharmacol., 609 (1982) p. 1374–81) or L-asparaginase (Uren, J. r. et al.; Canc. Research 39 (1979) p. 1927–33), or (iii) natural or synthetic hormones.

In the presently best developed and therefore also currently best preferred mode of the invention, the tolerogen is a covalent conjugate between monomethoxypolyethylene glycol (mPEG) with molecular weight in the range of 4,500–10,000 daltons and a foreign protein such as ovalbumin (OA), which served as a model protein. According to this modality, tolerogens of appropriate composition (i.e. consisting of the genetic material or its expression product and an optimal number of mPEG chains attached to it covalently) substantially suppress the formation of antibodies of different classes (e.g. IgE and IgG) which are directed specifically against the genetic material per se and/or against its expression product(s). The latter case is exemplified by OA or its covalent derivative with a number of 2,4-dinitrophenyl groups (DNP), i.e. OA-$DNP_n$, where n represents the average number of DNP groups coupled per one OA molecule.

Animal Model

The acceptability of the mouse as an experimental model for correlation to human utility in the present experiments is evidenced by Dreborg et al. "Immunotherapy with Monomethoxypolyethylene Glycol Modified Allergens". page 325, which indicates that similar results were achieved in humans and mice and thus confirms mice are an acceptable experimental model for evaluation of mPEG-modified allergens. See also *Antibodies: A Laboratory Manual*, Cold Spring Harbor Press, 1988, p. 93, which indicates that laboratory mice are an acceptable experimental animal model for examining the immune response, and that mice, in particular, possess appropriate characteristics for studies of the genetics of the immune response.

The Tolerogen Employed

As water-soluble polymers to be used for the preparation of a tolerogen, polyethylene glycols, having molecular weights in the range of 2,000 to 35,000, have proved to be effective. Polyethylene glycols in this context also include physiologically acceptable derivatives thereof, such as mono-alkyl ethers, preferably the monomethyl ether, whereby the remaining single terminal hydroxyl groups of the molecules are conveniently used for coupling to the protein.

Also other water-soluble polymers (macromolecules) may be used, such as polyvinylalcohols, polyvinylpyrrolidones, polyacrylamides and homo- as well as hetero-polymers of amino acids, polysaccharides (e.g. pullulan, inulin, dextran and carboxymethyl cellulose) or physiologically acceptable derivatives of these polymers.

For the covalent coupling of such polymers to the genetic material or its antigenic expression molecules, chemical methods normally used for coupling of biologically active materials to polymers may be used. Such methods include coupling by means of mixed anhydride, cyanuric chloride, isothiocyanate, reaction between SH derivatives and $CH_2I$ derivatives of the reacting molecules. However, it is obvious to the workers skilled in the art that other appropriate chemical methods may be used to lead to the production of conjugates of desired compositions.

The coupling reaction is made between active groups in the antigen molecules and in the polymer molecules. If necessary such groups may have to be introduced into said molecules before the coupling reaction. Such active groups are for example —$NH_2$, —NCS, —SH, —OH, —$CH_2I$ and COOH and they may be introduced according to well-known methods, if not already present in the molecules used for the production of tolerogenic conjugates.

In order to minimize the liberation in vivo of the immunogenic and/or allergenic constituent(s) of the tolerogenic conjugates and to maximize their effectiveness at a low dose, it is desirable that the covalent link between the water-soluble polymer and protein or its active derivative(s) should be as stable as possible under physiological conditions.

The coupling of the polymer onto the antigenic or genetic material must, as mentioned above, have been carried out to such an extent that the conjugate is rendered tolerogenic, as well as substantially non-allergenic and substantially non-immunogenic. In other words the tolerogens must retain a certain number of epitopes of the unmodified antigen, as long as their immunogenicity has been decreased to that they do not induce the formation of antibodies which may cause unacceptable adverse reactions.

To achieve tolerogenicity, the degree of substitution, also referred to as the degree of conjugation, which is defined as the number of polymer molecules coupled per antigen molecule, varies from one antigen molecule to another depending on the nature and size of the antigen and on the polymer and its molecular weight. Therefore, for the synthesis of a tolerogenic conjugate of a given antigen it is essential to synthesize a series of conjugates with different degrees of substitution and then establish the special range wherein the above mentioned requirements are fulfilled. Too low a degree of substitution may result in conjugates still endowed with allergenic and immunogenic properties, and too high a degree of substitution may result in conjugates which are not tolerogenic. One of skill in the relevant art will be able to optimize the degree of substitution using the disclosure as example. The optional substitution range is one in which tolerogenicity is achieved. One of skill in the art can perform the steps outlined in the specification and arrive at the appropriate degree of coupling of the nonimmunogenic polymer onto the antigenic protein so as to achieve the claimed properties.

In view of the finely tuned homeostatic balance of the immune response, which may be easily perturbed either upwards or downwards by the administration of a given antigen depending on its dose, state of aggregation and route of administration, as well as the presence or absence of adjuvants, it is critical when practicing the invention for treatment of appropriate disease conditions, that the tolerogenic conjugates be administered in such a manner as to lead to the down-regulation of the immune response with respect to one or more classes of immunoglobulins directed against the unconjugated biologically active product of the genetic material. Hence, in practicing this invention for treatment of appropriate diseases, the tolerogenic conjugates are to be injected in absence of adjuvants since the adjuvants may counteract their suppressogenic effects. However, the inclusion of adjuvants along with the unconjugated immunogenic material in the examples given below was justified so as to stimulate in experimental animals the enhanced production of antibodies in a relatively short time and to thus test under more stringent conditions the capacity of the tolerogenic conjugates to suppress the immune response in these animals even under these extreme conditions which are particularly favorable for enhancing the immune response.

The Foreign Genetic Material or Vehicle

In the claims and in the specifications, proteins and polypeptides are used synonymously. In the present context and claims the term foreign genetic material refers to a nucleotide, DNA, RNA, mRNA, plasmid, which are used as carriers of the gene and/or the gene itself responsible for the expression of the appropriate protein or protein derivative (fragments included), which are substantially immunogenic in the animal to be treated.

According to one aspect of the invention the genetic material should be therapeutically effective. Many such proteins, vectors, DNA are known per se (Culver, K. W., "Gene Therapy", 1994, p. xii, Mary Ann Liebert, Inc., Publishers, New York, N.Y., incorporated herein by reference in its entirety). For the purposes of example only, vectors may be selected from the group consisting of Moloney murine leukemia virus vectors, adenovirus vectors with tissue specific promoters, herpes simplex vectors, vaccinia vectors, artificial chromosomes, receptor mediated gene delivery, and mixtures of the above vectors. Gene therapy vectors are commercially available from different laboratories such as Chiron, Inc., Emeryville, Calif.; Genetic Therapy, Inc., Gaithersburg, Md.; Genzyme, Cambridge, Mass.; Somatx, Almeda, Calif.; Targeted Genetics, Seattle, Wash.; Viagene and Vical, San Diego, Calif.

The effective doses (amounts) and formulations commonly used are also known and may be applied to the present invention, although the invention potentially may employ reduced or increased doses. In principle, both the biologically active foreign genetic material or its derivatives, as well as the corresponding tolerogenic conjugates, may be administered parenterally in a soluble form in isotonic solution and after removal of aggregates by centrifugation. Moreover, to destroy unwanted cells, such as cancer cells or the host's cytotoxic cells responsible for auto-immune diseases, one may insert genetic material consisting in tandem of the DNA specific for the carrier of the bullet (e.g., an antibody molecule directed to a cell marker) and the DNA representing the bullet (e.g., toxins represented by ribosome inactivating proteins) into the patient.

Time Intervals for the Administration

For the induction of immunological tolerance to a given protein the protocol followed according to the invention comprises the administration initially of an immunosuppressively effective dose (amount) of tolerogen, which is given prior to the administration of the therapeutically active protein or its product. If necessary, this dose may be portioned and given on repeated occasions. The immunosuppressive dose which is given may vary from tolerogen to tolerogen, but it has to be administered prior to the entry of the protein into the host's system. According to the principles outlined in the examples, the practitioner skilled in the art can determine the variables such as dose of tolerogen and the minimum interval of time between its administration and the appearance of the immunogenic protein in the host's system. See, for example, references discussed in background of the invention. However, it is to be expected that gene therapy, resulting in the production of a "new" protein in the protein-deficient patient, has to be preceded by administration of the specific tolerogenic conjugate, i.e., the conjugate comprising the same protein and capable of suppressing selectively the immune response of the host with respect to the protein in question.

A time period of at least one day prior to the administration of the foreign genetic material is preferred, if not even mandatory. In a more preferred embodiment, the tolerogenic conjugate is administered at least seven days prior to administration of the foreign genetic material. The immunosuppressive dose refers to the amount of tolerogen required to substantially reduce the immune response of the patient to the protein or to its derivative(s) which will be produced as a result of the gene therapy. According to one mode of the invention, further doses of the tolerogen may be given in conjunction with the protein or its derivative(s), i.e. after the primary administration of the tolerogen. This mode may represent one way of sustaining the suppression and may offer a more efficient therapeutic regimen for the disease condition for which the treatment has been designed.

Figure 2:
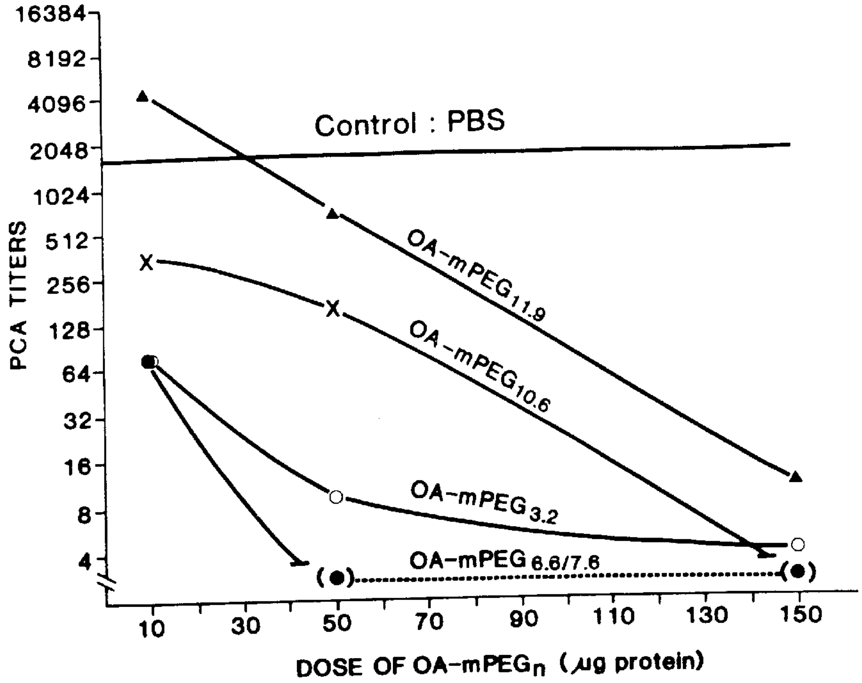
FIG. 2 is a diagram illustrating the suppressogenic relationship between the treatment of (B6D2)F1 mice with different dosages of OA-mPEG conjugates of different molecular compositions and the primary anti-OA IgG response, as measured by PCA titers.
Figure 3:
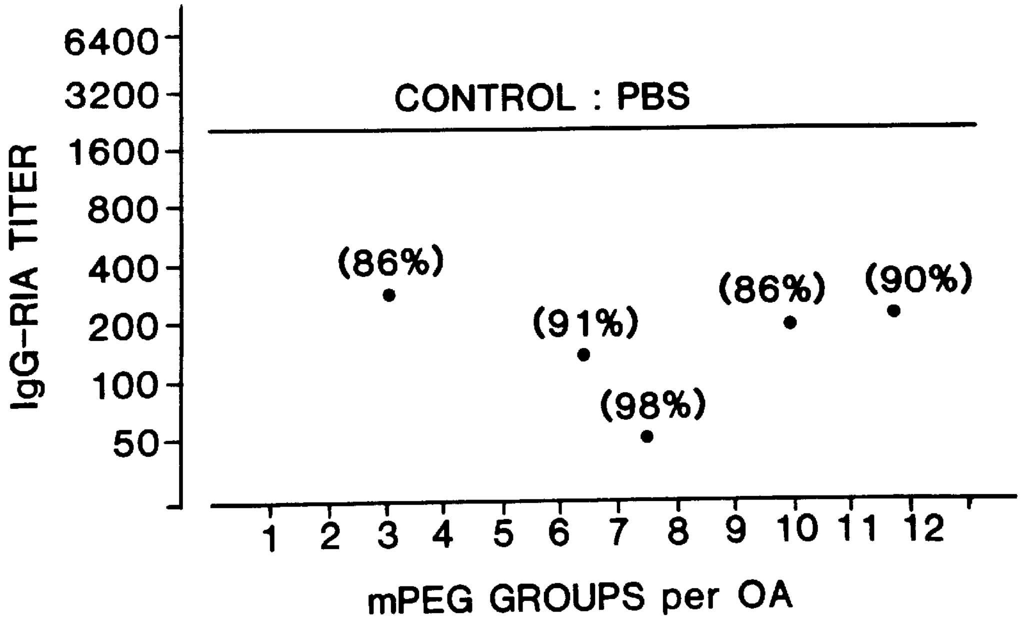
FIG. 3 is a diagram illustrating the suppressogenic relationship between the treatment of (B6D2)F1 mice with OA-mPEG conjugates of different molecular compositions and the primary anti-OA IgG, as measured by radioimmunoassay employing the paper radio immunosorbent procedure. The percentages in brackets represent the degree of suppression with respect to the minimal immune response in animals receiving phosphate buffered saline (PBS) in lieu of the conjugates.

The invention will now be illustrated by some non-limiting examples wherein OA and its tolerogenic mPEG derivatives have been applied as model substances to confirm the usefulness of the proposed immunosuppressive treatment of a well-established animal model commonly utilized in the field of immunology, The conjugates will be designated as OA-$(mPEG)_n$ where n represents the average degree of conjugation. FIGS. 1, 2 and 3 show diagrams illustrating the efficiency of the invention. The percentages in brackets of FIGS. 1 and 3 represent the degree of suppression with respect to the minimal immune response in animals receiving phosphate buffered saline (PBS) in lieu of the conjugates.

EXAMPLE 1

Preparation of OA-mPEG Conjugates having Different Degrees of Substitution

The conjugates used in the experiments given below have been prepared by coupling mPEG molecules to OA essentially according to the procedure described by Abuchowski et al. (*J. Biol. Chem.* 252, 3518, 1977 utilizing cyanuric chloride as one of the possible coupling agents. To begin with, in the experiment described the "active intermediate" consisting of an mPEG molecule attached to cyanuric chloride was prepared.

It was found that the most important condition of this reaction was that all reagents be completely anhydrous and that the reaction mixture be protected from atmospheric moisture because of its high susceptibility to hydrolysis. Among various methods used for the synthesis of the "active intermediate", the example given below illustrates the general procedure. (See also Jackson, C. -J. C., Charlton, J. L., Kuzminski, K., Lang, G. M. and Sehon, A. H. "Synthesis, isolation and characterization of conjugates of ovalbumin with monomethoxypolyethylene glycol using cyanuric chloride as the coupling agent. *Anal. Biochem.* 165: 114, 1987, incorporated herein by reference in its entirety.)

Monomethoxypolyethylene glycol (2.5 g. mol wt 5590, Union Carbide) was dissolved with warming in anhydrous benzene (40 ml) and a portion of the benzene (20 ml) was removed by distillation to azeotrope off any water in the polymer. Cyanuric chloride [$(CNCl)_3$, 0.83 g, Aldrich, recrystallized from benzene] was added under nitrogen followed by potassium carbonate (0.5 g. anhydrous powdered) and the mixture stirred at room temperature for 15 hours. The mixture was then filtered under dry nitrogen and the filtrate mixed with anhydrous petroleum ether (ca 50 ml, b.pt. 30–60° C.) in order to precipitate the polymer. The polymer was separated by filtration under nitrogen, dissolved in benzene (20 ml) and reprecipitated with petroleum ether. This process was repeated seven times to insure that the polymer was free of any residual cyanuric chloride. The active intermediate was finally dissolved in benzene, the solution frozen and the benzene sublimed away under high vacuum to leave a fine white powder.

Elemental analysis of the intermediate confirmed that it contained 2 chlorine atoms. The intermediate, corresponding to $C_{256.3}H_{307.7}O_{127.2}N_3Cl_2$ with an average molecular weight of 5,738 daltons would have a theoretical composition in percentages of C, 53.65; H, 8.92; N, 0.73; Cl, 1.24;

which agrees with its determined composition of C, 53.51; H, 8.89; N, 0.77; Cl, 1.08.

The chloride content of the intermediate was also determined by hydrolysis and titration of the chloride released with silver nitrate. Thus, the activated intermediate (120 mg) was dissolved in water (10 ml) and the pH adjusted to 10 with dilute sodium hydroxide. After heating at 90° C. for two hours, the solution was cooled and the chloride titrated with silver nitrate (0.001N), using a chloride ion selective electrode to indicate the endpoint. The chloride content of the activated intermediate was found to be 2.1, consistent with the structure shown above.

The OA [40 mg, purified by chromatography on Ultrogel® AcA-54 (LKB, Bromma, Sweden)] was dissolved in sodium tetraborate buffer (4 ml, 0.1 M, pH 9.2) and the activated mPEG added to the solution at 4° C. The amount of activated mPEG was varied to prepare conjugates of differing degrees of polymer substitution. Mole ratios (mPEG/OA) used to prepare specific conjugates are given in Table 1. The polymer-protein mixture was stirred for one half hour at 4° C. and then one half hour at room temperature. The reaction mixture was desalted by either dialyzing for four days against running distilled water or by passing through a column of Sephadex® G-25 (Pharmacia Fine Chemicals AB, Uppsala, Sweden).

A DEAE-cellulose or DEAE-Sephacryl® (Pharmacia Fine Chemicals AB, Uppsala, Sweden) column (5 cm by 30 cm) was equilibrated with phosphate buffer (0.008 M, pH 7.7). The salt free OA conjugates were applied in water and the free (unbound) mPEG washed through the column with the pH 7.7 buffer. Free mPEG was detected on thin layer chromatography [Camag (Kieselgel DSF-5, Terochem Lab Ltd, Alberta) eluant 3:1 chloroform/methanol] using iodine vapor for development. After removal of the free mPEG from the ion-exchange column, sodium acetate buffer (0.05 M, pH 4.0) was used to elute the conjugate. The conjugate fractions were dialyzed and lyophilized to give the dry conjugates.

TABLE 1

Preparation of OA-$mPEG_n$ Conjugates

| Conjugates[a] | Preparation ratio[b] | % mPEG[c,e] | % OA[d,e] |
|---|---|---|---|
| OA-$mPEG_{3.2}$ | 10:1 | 26 | 70 |
| OA-$mPEG_{6.6}$ | 25:1 | 36 | 47 |
| OA-$mPEG_{7.6}$ | 25:1 | 42 | 47 |
| OA-$mPEG_{10.6}$ | 50:1 | 51 | 41 |
| OA-$mPEG_{11.9}$ | 50:1 | 52.4 | 38 |

[a]The degree of substitution, n, is calculated by the formula $$\frac{\%\ \text{mPEG}}{\%\ \text{OA}} \times \frac{\text{mol wt OA}}{\text{mol wt mPEG}}$$

[b]Mole ratio mPeg:OA based on a molecular weight of 5.740 for mPEG-dichlorocyanurate and 44.460 daltons for OA.
[c]The percentages of mPEG by weight were determined by nuclear magnetic resonance (NMR).
[d]The percentages of protein by weight were determined by the biuret method.
[e]The total compositions of the conjugates, as calculated form the NMR and biuret analysis, are only of the order of 90% of the samples by weight; the difference of the order of 10% attributed to moisture absorbed by the conjugates and/or to small amounts of DEAE-cellulose leaching from the column.

EXAMPLE 2

Determination of the Immunosuppressive Effect on the IqE Response of Different OA-$mPEG_n$ Conjugates The results of experiments illustrated in FIG. 1 clearly demonstrate the stringent dependency of the suppressogenicity of mPEG conjugates on their molecular composition. Thus, whereas treatment of groups of four (B6D2)F1 mice each with 50 μg of OA-$mPEG_{3.2}$, or OA-$mPEG_{6.6}$, or OA-$mPEG_{7.6}$ one day prior to intraperitoneal immunization with the sensitizing dose, consisting of 1 μg of OA and 1 mg $Al(OH)_3$, led to essentially complete (99–100%) abrogation of the primary anti-OA IgE response, as measured—on day 14 after immunization—by PCA in hooded rats, the more substituted conjugates, i.e. OA-$mPEGI_{10.6}$ and OA-$mPEG_{11.9}$, inhibited the anti-OA IgE response, respectively, only to the extent of 94% and 50%. In this and the following examples, the weights of the conjugates given correspond to their protein content.

EXAMPLE 3

Long Lasting Suppression of the IgE Response by Protein-mPEG Conjugates in Contrast to a Transient Suppressive Effect of Unconjugated Protein It is to be noted that even unmodified OA was capable of downregulating the primary IgE response in relation to the response of control mice which had received PBS instead of OA or conjugates. In this experiment three groups of four (B6D2)F1 mice each received phosphate buffered saline, or 50 μg of OA-$mPEG_{4.5}$ or 50 μg of OA. All animals were bled on day 10, 14, 21, 27, 35, 42 and 49 and their IgE titers were determined by PCA in hooded rats. As illustrated in Table 2, it is important to point out that whereas the suppressogenic effect of OA-mPEG conjugates was long-lasting, the downregulating effect of free OA was of short duration and, in actual fact, its administration predisposed the animals to an anamnestic response which reached, after booster immunization (administered on day 28), IgE antibody levels equivalent to those of control animals which had received PBS and the two sensitizing doses of one antigen. The results given in Table 2 clearly demonstrate that a tolerogenic conjugate injected prior to repeated administration of the corresponding free protein essentially abrogated the immune response.

TABLE 2

Effect of administering 50 μg of OA-$mPEG_{4.5}$ or of free OA one day prior to immunization

| Day of bleeding after primary immunization | PCA titers for groups of mice treated with PBS | OA | OA-$mPEG_{4.5}$ |
|---|---|---|---|
| 10 | 5,120 | 40 | <4 |
| 14 | 1,940 | 40 | <4 |
| 21 | 1,280 | 40 | <4 |
| 27 | 640 | 40 | <4 |
| 35 | 1,920 | 1,920 | 160 |
| 42 | 2,560 | 1,280 | 160 |
| 49 | 5,120 | N.D.* | 160 |

On day 28 all three groups received a booster dose of the sensitizing OA preparation.
*N.D. = not determined

EXAMPLE 4

The Effect of Different Doses of the Tolerogen on the IgE Response

Each OA-mPEG conjugate was injected into groups of 4 mice each at the four doses of 10 μg, 50 μg, 150 μg and 600 μg. The control group of mice received PBS as placebo.

As is evident from FIG. 2, treatment with different conjugates at doses of 10 μg and 50 μg per mouse revealed marked differences in their suppressogenic capacity. It is also to be noted that at a dose of 150 μg, all conjugates were highly suppressive and at 600 μg (data note shown) all the compounds tested suppressed completely the IgE response.

EXAMPLE 5

The Effect of Different Doses of the Tolerogen on the IgE Response

The sera used in FIG. 3 to illustrate the effect of tolerogenic conjugates on the IgG response were the same as those used in FIG. 1. As illustrated in FIG. 3, administration of 50 $\mu$g of OA-mPEG$_{7.6}$ resulted in the maximal suppression, i.e. of the order of 98% of the primary anti-OA IgG response, which was determined 14 days after the first injection of the sensitizing dose of OA by a radio-immunoassay employing the paper radio immunosorbent procedure (Kelly, K. A. et al.; J. Immunol. Meth. 39 (1980) p. 317–33) utilizing OA bound to the paper and with $_{125}$I-labelled affinity purified sheep antiserum to mouse IgG.

EXAMPLE 6

The Suppressive Effect of OA-mPEG$_{10}$ on IgM, IgG, and IgE Plaque forming Cells (PFC) in Spleen and Lymph Nodes.

One mg of OA-mPEG$_{10}$ (containing 10 mPEG groups with an average mol wt of 10,000 daltons, which were coupled per OA molecule by the succinic anhydride method (Wie, S. I. et al., Int. Archs. Allergy appl. Immun. 64, 84 (1981)) or PBS was administered intraperitoneally to each group of four (B6D2)F1 mice each one day prior to immunization with 1 $\mu$g of DNP$_3$-OA in 1 mg Al(OH)$_3$.

On several days thereafter the spleen, as well as the mesenteric, parathymic and inguinal lymph nodes were removed and assayed for IgM, IgG, and IgE anti-DNP PFC (Rector, E. S. et al. , Eur. J. Immunol. 10, p. 944–49 (1980). In Table 3 are given the numbers of PFC in the above tissues 10 days after immunization; from these data it is evident that treatment with this tolerogen markedly reduced the number of IgM, IgE, and IgG PFC in all tissues examined. Therefore, these results support the claim that the tolerogens shut off the immune response rather than neutralize the circulating antibodies.

TABLE 3

The effect of OA-mPEG$_{10}$ on the suppression of IgM, IgG and IgE plaque forming cells (PFC) in spleen and lymph nodes

| | | Anti-DNP PFC per $10^8$ cells from different tissues* | | | |
|---|---|---|---|---|---|
| Antibody Class | Treatment | Spleen | Parathymic Nodes | Mesenteric Nodes | Inguinal Nodes |
| IgM | PBS | 2,150 | 2,950 | Nd | Nd** |
| | OA-mPEG | 900 | 200 | Nd | Nd |
| IgG | PBS | 15,350 | 78,550 | 5,000 | Nd |
| | OA-mPEG | Nd | 1,300 | Nd | Nd |
| IgE | PBS | 10,410 | 16,530 | 11,140 | 300 |
| | OA-mPEG | 500 | 950 | 400 | Nd |

*Each tissue sampling represents a pool from 4 mice
**Nd = undetected

The above experiments establish the immunosuppressive effects discussed above and the effects at the various dosages.

EXAMPLE 7

In addition, utilizing the hu-PBL-SCID mice, it was demonstrated that in accordance with the phenomenon of "linked immunological suppression", cross-specific suppression of the human antibody response could be induced to murine mAbs which differ in their antigen binding specificities from those of the murine is which had been incorporated into the tolerogenic conjugates, on condition that both mAbs shared the same heavy and light chains. Thus, that pan-specific suppression of the "human" antibody responses against murine monoclonal antibodies (i.e., HAMA responses) of the IgG class could be achieved with 8 tolerogenic mPEG preparations, each consisting of one of the 4 gamma chains and of one of the two types of light chains of murine IgG (Bitoh, S., Lang, G. M., Kierek-Jaszczuk, D., Fujimoto, S. and Sehon, A. H. Specific immunosuppression of human anti-murine antibody (HAMA) responses in hu-PBL-SCID mice. Hum. Antibod. Hybridomas 4:144–151, 1993).

The utility of this technology for therapeutic strategies in man, which necessitate the administration of immunogenic Biological Response Modifiers (BRMs), is apparent.

The safety of administration of MPEG conjugates of different allergenic proteins has been established in clinical trials in a number of countries in close to 300 patients afflicted by a variety of allergies medicated by IgE antibodies (Dreborg, S. and Akerblom, E. Immunotherapy with monomethoxypolyethylene glycol modified allergens. In: S. D. Bruck (Ed.), CRC Crit. Rev. Ther. Drug Carrier Syst. 6:315–363, (1990)).

It is to be emphasized that the function of the mPEGylated protein in the present strategy is to induce Suppressor T (Ts) cells which recognize the epitopes shared by both the unmodified and the mPEGylated BRM. In other words, this technology leads to conversion of antigens not only to nonimmunogenic, but most importantly to actively immunosuppressive molecules, which induce immunologic tolerance with respect to the original unmodified protein antigen. By contrast, the purpose of some other workers and companies utilizing mPEG conjugates of BRMs is to only reduce their immunogenicity i.e., without converting them to active tolerogens, and to thus only increase their half-life in circulation.

The discovery that pretreatment of a host with tolerogenic mPEG conjugates of a given protein Ag, followed by administration of the unmodified Ag, results in abrogation of the host's capacity to mount an antibody response to the Ag in question has a direct utility in some forms of "gene therapy" which would result in the production of the protein corresponding to the gene in question, on condition that the host would have been deficient of the gene responsible for the expression of the particular protein from birth (see, Sehon, A. H. Suppression of antibody responses by chemically modified antigens, Carl Prausnitz Memorial Lecture, XVIII Symposium Collegium Internationale Allergologicum, *Int. Arch. Allergy appl. Immunol.* 94:11–20, 1991; Takata, M., Maiti, P. K., Kubo, R. T., Chen, Y-H. Holford-Stevens, V., Rector, E. S. and Sehon, A. H. Cloned suppressor T cells derived from mice tolerized with conjugates of antigen and monomethoxypolyethylene glycol. *J. Immunol.* 145:2846–2853, 1990; and Takata, M., Maiti, P. K., Bitoh, S., Holford-Stevens, V., Kierek-Jaszczuk, D., Chen, Y., Lang, G. M. and Sehon, A. H. Downregulation of helper T cells by an antigen-specific monoclonal Ts factor. *Cell. Immunol.* 137:139–149, 1991).

On the basis of well known immunological principles, it would be obvious that in conditions when the host is totally deficient, from birth, of the gene which has to be inserted after the maturation of the immune system, the protein expressed by the gene in question induces in the host an immune response against itself, (since the host with a normal immune system would not have been rendered from birth tolerant to the protein in question). Thus, (i) the immune response of the host to this protein would be manifested in the production of antibodies or cytotoxic cells by the host to the "new" protein, and (ii) this immune response would not only neutralize the "new" protein, but may also lead to diverse therapeutic complications due to formation of "immune complexes" consisting of the resulting antibody-antigen aggregates.

Clearly, the one condition for which gene therapy has proven to be an effective therapeutic modality is adenosine deaminase (ADA) deficiency, which results in the impairment of T lymphocytes and hence in the severe combined immunodeficiency disorder (SCID) in children deficient of ADA from birth. Therefore, it is not surprising that Dr. Culver was successful in developing a curative gene therapy for this condition by treating the SCID kids by infusion of their own "ADA gene-corrected cells".

However, unless gene therapy is instituted from birth, when it is relatively easier to induce immunological tolerance to a foreign genetic material or its expressed products, than in adulthood after maturation of the immune system, the success of gene therapy in hosts with a well formed immune system would be undermined by the above-mentioned complications. Hence, to avoid these complications, the induction of immunological tolerance to a well-defined protein Ag, by pretreatment of the host with tolerogenic mPEG conjugates of the corresponding Ag, i.e., $Ag(mPEG)_n$, is indispensable for the success of gene therapy in disease conditions, when the same protein is expressed by the inserted gene, since this protein would induce deleterious immune response against itself in the host.

The present invention is the confirmation and extension of the earlier discovery of induction of immunological tolerance by immunosuppressive $Ag(mPEG)_n$ conjugates to therapies involving the insertion of new genes into the host with an intact immune system.

EXAMPLE 8

Thus, in accordance with the present invention, prior to beginning of gene therapy, i.e., prior to insertion of a new gene into a host which is required for expression of a protein beneficial to the host, e.g., one of the deficient clotting factors or enzymes, it is essential to render the host tolerant to the protein in question by the use of the invention described.

EXAMPLE 9

The expressed protein material of the cystic fibrosis transmembrane conductance regulatory gene (CFTR) (Genzyme, Cambridge, Mass.) for the treatment of cystic fibrosis is dissolved in sodium tetraborate buffer (4 ml, 0.1 M, pH 9.2) and the activated mPEG added to the solution at 4° C. The amount of activated mPEG is varied to prepare conjugates of differing degrees of polymer substitution. Different mole ratios (mPEG/gene product) are used to prepare specific tolerogenic conjugates as described earlier. The polymer-gene product mixture is stirred for one half hour at 4° C. and then one half hour at room temperature. The reaction mixture is desalted by either dialyzing for four days against running distilled water or by passing through a column of Sephadex® G-25 (Pharmacia Fine Chemicals AB, Uppsala, Sweden).

A DEAE-cellulose or DEAE-Sephacryl® (Pharmacia Fine Chemicals AB, Uppsala, Sweden) column (5 cm by 30 cm) is equilibrated with phosphate buffer (0.008 M, pH 7.7). The salt free mPEG conjugates of the cystic fibrosis gene product are applied in water and the free (unbound) mPEG washed through the column with the pH 7.7 buffer. Free mPEG is detected on thin layer chromatography [Camag (Kieselgel DSF-5, Terochem Lab Ltd, Alberta) eluant 3:1 chloroform/methanol] using iodine vapor for development. After removal of the free mPEG from the ion-exchange column, sodium acetate buffer (0.05 M, pH 4.0) is used to elute the conjugate. The conjugate fractions are dialyzed and lyophilized to give the dry conjugates.

Conjugates of the CFTR gene are administered to a patient at least one day prior to transfer of the cystic fibrosis transmembrane conductance regulator gene to lung tissue using recombinant adenoviral vectors or liposomes.

EXAMPLE 10

The expressed protein material of the low density lipoprotein receptor (LDLr) gene used in the treatment of familial hypercholesterolemia is dissolved in sodium tetraborate buffer (4 ml, 0.1 M, pH 9.2) and the activated mPEG added to the solution at 4° C. The amount of activated mPEG is varied to prepare conjugates of differing degrees of polymer substitution. Different mole ratios (mPEG/gene product) is used to prepare specific tolerogenic conjugates as described earlier. The polymer-gene product mixture is stirred for one half hour at 4° C. and then one half hour at room temperature. The reaction mixture is desalted by either dialyzing for four days against running distilled water or by passing through a column of Sephadex® G-25 (Pharmacia Fine Chemicals AB, Uppsala, Sweden).

A DEAE-cellulose or DEAE-Sephacryl® (Pharmacia Fine Chemicals AB, Uppsala, Sweden) column (5 cm by 30 cm) is equilibrated with phosphate buffer (0.008 M, pH 7.7). The salt free mPEG conjugates of the LDLr-gene products are applied in water and the free (unbound) mPEG washed through the column with the pH 7.7 buffer. Free mPEG is detected on thin layer chromatography [Camag (Kieselgel DSF-5, Terochem Lab Ltd, Alberta) eluant 3:1 chloroform/methanol] using iodine vapor for development. After removal of the free mPEG from the ion-exchange column, sodium acetate buffer (0.05 M, pH 4.0) is used to elute the conjugate. The conjugate fractions are dialyzed and lyophilized to give the dry conjugates.

Conjugates of the LDLr gene product are administered to a patient. Hepatocytes are grown in the laboratory and genetically altered with a murine retroviral vector containing LDLr gene. The cells are reinfused through the hepatic artery to the liver of the patient at least one day after administration of the conjugate.

Table 4 shows a list of gene therapy systems which have been approved by the Recombinant DNA Activities Committee of the National Institutes of Health. However, no consideration appears to have been given to overcoming the potential complications due to the host mounting an immune response against the respective gene products. Clearly, if the patient had been producing from birth these proteins, he/she would be tolerant to them, i.e., and gene therapy would not necessitate the strategy of the described invention if the patient has retained his/her tolerance between the shutting off of his/her own genes producing the desired protein and the time of initiation of gene therapy by transfer of the gene in association with an appropriate "vehicle" for the renewed production of the protein.

| Disorder (gene used) | Cells altered (vector) |
|---|---|
| Adenosine deaminase deficiency[a] (ADA) | T-cells and stem cells (retroviral) |
| Brain tumors (MDR-1) | Stem cells (retroviral) |
| Brain tumors (primary and metastatic) (HS-tk) | Tumor cells (retroviral) |
| Brain tumors (primary)[a] (HS-tk) | Tumor cells (retroviral) |
| Brain tumors (primary and metastatic) (HS-tk) | Tumor cells (retroviral) |
| Brain tumors (primary and metastatic) (HS-tk) | Tumor cells (retroviral) |
| Brain tumors (primary) (anti-sense IGF-1) | Tumor cells (DNA transfection) |
| Brain tumors (primary)[a] (HS-tk) | Tumor cells (retroviral) |
| Brain tumors (primary and metastatic) (HS-tk) | Tumor cells (retroviral) |
| Breast cancer (IL-4) | Fibroblasts (retroviral) |
| Breast cancer (MDR-1) | Stem cells (retroviral) |
| Breast cancer (MDR-1) | Stem cells (retroviral) |
| Colorectal cancer (IL-4) | Fibroblasts (retroviral) |
| Colorectal cancer (IL-2 or TNF-α gene) | Tumor cells (retroviral) |
| Colorectal cancer (HLA-B7 and β2-microglobulin) | Tumor cells (liposomes) |
| Colorectal cancer (IL-2) | Fibroblasts (retroviral) |
| Cystic fibrosis[a] (CF TR) | Respiratory epithelium (adenoviral) |
| Cystic fibrosis[a] (CF TR) | Respiratory epithelium (adenoviral) |
| Cystic fibrosis (CF TR) | Respiratory epithelium (liposomes) |
| Cystic fibrosis[a] (CF TR) | Respiratory epithelium (adenoviral) |
| Cystic fibrosis[a] (CF TR) | Respiratory epithelium (adenoviral) |
| Cystic fibrosis[a] (CF TR) | Respiratory epithelium (adenoviral) |
| Familial hypercholesterolemia[a] (LDLr) | Liver cells (retroviral) |
| Gaucher disease[a] (glucocerebrosidase) | Stem cells (retroviral) |
| Gaucher disease[a] (glucocerebrosidase) | Stem cells (retroviral) |
| Gaucher disease[a] (glucocerebrosidase) | Stem cells (retroviral) |
| Gaucher disease (glucocerebrosidase) | Stem cells (retroviral) |
| HIV infection (Mutant Rev) | T cells (retroviral) |
| HIV infection (HIV-1 III env) | Muscle (retroviral) |
| HIV infection (HIV-1 IIIB Env and Rev) | Muscle (retroviral) |
| HIV infection (HIV-1 ribozyme) | T cells (retroviral) |
| Leptomeningeal carcinomatosis (HS-tk) | Tumor cells (retroviral) |
| Malignant melanoma (IL-4) | Tumor cells (retroviral) |
| Malignant melanoma (IL-2) | Tumor cells (retroviral) |
| Malignant melanoma (IL-2) | Tumor cells (retroviral) |
| Malignant melanoma (IL-2) | Tumor cells (retroviral) |
| Malignant melanoma (IL-4) | Fibroblasts (retroviral) |
| Malignant melanoma (HLA-B7) | Tumor cells (liposomes) |
| Malignant melanoma (HLA-B7 and $\beta_2$-microglobulin) | Tumor cells (liposomes) |
| Malignant melanoma (TNF-α or IL-2) | T cells or tumor cells (retroviral) |
| Malignant melanoma (interferon-γ) | Tumor cells (retroviral) |
| Malignant melanoma (B7) | Tumor cells (retroviral) |
| Neuroblastoma[a] (IL-2) | Tumor cells (retroviral) |
| Non-small cell lung cancer (p53 or antisense K-ras) | Tumor cells (retroviral) |
| Ovarian cancer (HS-tk) | Tumor cells (retroviral) |
| Ovarian cancer (MDR-1) | Stem cells (retroviral) |
| Ovarian cancer (MDR-1) | Stem cells (retroviral) |
| Renal cell carcinoma (IL-2) | Tumor cells (retroviral) |
| Renal cell carcinoma (IL-4) | Fibroblasts (retroviral) |
| Renal cell carcinoma (TNF-α or IL-2) | Fibroblasts (retroviral) |
| Renal cell carcinoma (GM-CSF) | Tumor cells (retroviral) |
| Small cell lung cancer (IL-2) | Tumor cells (DNA transfection) |
| Solid tumors (HLA-B7 and β2-microglobulin) | Tumor cells (liposomes) |

Table 5 shows a list of health disorders for which chromosomal locations are known which are considered treatable by gene therapy.

| Disorder | Location |
|---|---|
| A | |
| 11-Beta-hydroxysteroid dehydrogenase deficiency (1) | Chr.1 |
| 3-Beta-hydroxysteroid dehydrogenase, type II, deficiency (3) | 1p13.1 types (1) |
| 3-Hydroxyacyl-CoA dehydrogenase deficiency (1) | Chr.7 |
| 3-Ketothiolase deficiency (1) | 11q22.3-q23.1 |
| Aarskog-Scott syndrome (2) | Xp11.21 |
| ?Abetalipoproteinemia (1) | 2p24 |
| [Acanthocytosis. one form] (1) | 17q21-q22 |
| Acatalasemia (1) | 11p13 |
| Acetyl-CoA carboxylase deficiency (1) | 17q21 |
| Acid-maltase deficiency, adult (1) | 17q23 |
| Acoustic neuroma (2) | 22q12.2 |
| ?Acrocallosal syndrome | 12p18.3-p11.2 |
| ACTH deficiency (1) | 2p25 |
| Acyl-CoA dehydrogenase, long chain, deficiency of (1) | 2q34-q35 |
| Acyl-CoA dehydrogenase, medium chain, deficiency of (1) | 1p31 |
| Acyl-CoA dehydrogenase, short chain, deficiency of (1) | 12q22-qter |
| Adenylosuccinase deficiency (1) | 22q13.1 |
| Adrenal hyperplasia, congenital, due to 11-beta-hydroxylase deficiency (1) | 8q21 |
| Adrenal hyperplasia, congenital, due to 21-hydroxylase deficiency (3) | 6p21.3 |
| Adrenal hyperplasia V (1) | 10q24.3 |
| Adrenal hypoplasia, primary (2) | Xp21.3-p21.2 |
| Adrenocortical carcinoma (2) | 11p15.5 |
| Adrenocortical carcinoma, heriditary (2) | 11p15.5 |
| Adrenoleukodystropy (2) | Xq23 |
| Adrenomyeloneuropathy (2) | Xq23 |
| [APP deficiency, congenital] (1) | 4q11-q13 |
| Agammaglobulinemia, type 1, X-linked (3) | Xq21.3-q22 |
| Agammaglobulinemia, type 2, X-linked (2) | Xp22 |
| Aicardi syndrome (2) | Xp22 |
| Alagille syndrome (2) | 20p11.2 |
| Albinism (3) | 11q14-q21 |
| Albtalma, brown, 203294 (1) | 9p23 |
| Albinism, oculoeutaneous, type II (3) | 15q11.1-q12 |
| Albinism-deafness syndrome (2) | Xq26.3-q27.1 |
| ?Albright hereditary osteodystrophy-2 (2) | 15q11-q18 |
| ?Aldolase A deficiency (1) | 16q22-q24 |
| Aldosteroslam, glacocorticoid-remediable (1) | 8q31 |
| Allan-Herndon syndrome (2) | Xq21 |
| Alpha-1-antichymetrypsin deficiency (1) | 14q32.1 |
| Alpha-NAGA deficiency (1) | 22q11 |
| Alpha-thalassemia/mental retardation syndrome, type 1 (1) | 16pter-p13.3 |
| Alpha-thalassemia/mental retardation syndrome, type 2 (2) | Xq12-q21.31 |
| Alport syndrome, 301050 (3) | Xq22 |
| Alveolar proteinois, congenital, 265120 (1) | Chr.2 |
| Alzheimer disease, APP related (3) | 21q21.3-22.05 |
| ?Alzheimer disease-1 (2) | 21q |
| Alzheimer disease-3 (3) | 14q24.3 |
| Alzheimer disease-2, late onset (2) | 19cen-q13.2 |
| Amelogenesis imperfecta (1) | Xp22.3-p22.1 |
| ?Amelogenesis imperfecta-3, hypoplastic type (2) | Xq22-q28 |
| [AMP deaminase deficiency, erythrocyte] (1) | 1p21-p13 |
| Amyloid neuropathy, familial, several allelic | 18q11.2-q12.1 |
| Amyloidosis, cerebroarterial, Dutch type (1) | 21q21.3-q22.05 |
| Amyloidosis, Finnish type, 105120 (1) | 9q34 |
| Amyloidosis, hereditary renal, 105200 (1) | 4q28 |
| Amyloidosis, Iowa type, 107680.0010 (1) | 11q23 |
| [?Amyloidosis, secondary, susceptibility to] (1) | 1q21-q23 |
| Amyloidosis, senile systemic (1) | 18q11.2-q12.1 |
| Amyotrophic lateral scierosis, juvenile (2) | 2q33-q35 |
| Amytrophic lateral scierosis, one form, 105400 (3) | 21q22.1 |
| ?Anal canal carcinoma (2) | 11q22-qter |
| Analbuminemia (1) | 4q11-q13 |
| ?Anemia, megalobiastic, due to DHFR deficiency (1) | 5q11.2-q13.2 |
| Anemia, pernicious, congenital, due to deficiency of intrinsic factor (1) | Chr.11 |
| ?Anemia, sideroblastic, with spinocerebellar ataxia (2) | Xq13 |
| Anemia, sideroblastic/hypochromic (3) | Xp11.21 |

-continued

| Disorder | Location |
|---|---|
| Aneurysm, familail, 100070 (1) | 2q31 |
| Angelman syndrome (2) | 15q11-q13 |
| Angiodema, hereditary (1) | 11q11-q13.1 |
| Anhidrotic ectodermal dysplasia (2) | Xq12.2-13.1 |
| Aniridia of WAGR syndrome (2) | 11p13 |
| Aniridia-2 (3) | 11p13 |
| Ankylosing spondyitis (2) | 6p21.3 |
| ?Anophthalmos-1 (2) | Xp27-q28 |
| Anterior segment mesenchymal dysgenesis (2) | 4q28-q31 |
| Antithrombia III deficiency (3) | 1q23-q25 |
| ApoA-I and apaC-III deficiency, combined (1) | 11q23 |
| Apolipoprotein B-100, defective (1) | 2p24 |
| [Apolipoprotein H deficiency] (1) | 17q23-qter |
| Argininemia (1) | 6q23 |
| Argininosuccinicaciduria (1) | 7cen-q11.2 |
| Aspartylglucosaminuria (3) | 4q23-q27 |
| Ataxia-telangiectasia (2) | 11q22-q23 |
| [Atherosclerosis, susceptibility to] (2) | 19p13.3-p13.2 |
| ?[Atherosclerosis, susceptibility to] (3) | 8p21-p12 |
| Atopy (2) | 11q12-q13 |
| Atransferrinemia (1) | 3q21 |
| Atrial septal defect, secundum type (2) | 6p21.3 |
| Autonomic failure due to DBH deficiency (1) | 9q34 |
| B | |
| Basal cell nervous syndrome (2) | 9q31 |
| Battern disease (2) | 16p12 |
| ?Battern disease, one form, 204200 (1) | 15q24-q25 |
| Becker muscular dystrophy (3) | Xp21.2 |
| Beckwith-Wiedemann syndrome (2) | 11pter-p15.4 |
| Bernard-Soulier syndrome (1) | 17pter-p12 |
| Biepharaphimosis, spicanthus inversus and ptosis (2) | 3q22-q23 |
| Bloom syndrome (2) | 15q26.1 |
| Borjeson-Forssmann-Lehmann syndrome (2) | Xq26-q27 |
| Bornholm eye disease (2) | Xq28 |
| Branchiootic syndrome (2) | 8q13.3 |
| ?Breast cancer (1) | 17p13.3 |
| Breast cancer (1) | 6q24-q27 |
| Breast cancer, ductal (2) | 1p36 |
| Breast cancer, ductal (2) | Chr.13 |
| Breast cancer-1, early onset (2) | 17q21 |
| Brody myopathy (1) | Chr.16 |
| Burkitt lymphoma (3) | 8q24.12-q24.13 |
| C | |
| ?Clq deficiency (1) | 1p36.3-p34.1 |
| Clr/Cls deficiency, combined (1) | 12p13 |
| C2 deficiency (3) | 6p21.3 |
| C3 deficiency (1) | 19p13.3-p13.2 |
| C3b inactivator deficiency (1) | 4q25 |
| C4 deficiency (3) | 6p21.3 |
| C5 deficiency (1) | 9q34.1 |
| C6 deficiency (1) | 5p13 |
| C7 deficiency (1) | 5p13 |
| C8 deficiency, type I (2) | 1p32 |
| C8 deficiency, type II (2) | 1p32 |
| C9 deficiency (1) | 5p13 |
| Campomelic dysplasia-1 (2) | 17q24.3-q25.1 |
| Carbamoylphosphate synthelase I deficiency (1) | 2p |
| [Carbonic anhydrase I deficiency] (1) | 8q22 |
| Carboxypeptidase B deficiency (I) | Chr.13 |
| ?Cardiomyopathy (1) | 2q35 |
| Cardiomyopathy, dilated, X-linked (I) | Xp21.2 |
| Cardiomyopathy, familial, hypertrophic, 1, 192600 | 14q12 |
| Cardiomyopathy, familial hypertrophic, 2 (2) | 1q8 |
| Cardiomyopathy, familial hypertrophic, 3 (2) | 15q2 |
| Cardlage-hair hypoplasia (2) | 9p13-q11 |
| Cat-eye syndrome (2) | 22q11 |
| !Cataract, anterior polar, I (2) | 14q24-qter |
| ?Cataract, congenital total (2) | Xp |
| Cataract, congenital, with microphthalmia (2) | 16p13.3 |
| Cataract, Coppock-like (3) | 2q33-q35 |
| Cataract, Maerner type (2) | 16q22.1 |
| Cataract, zonular pulverulent-1 (2) | 1q2 |
| CD3, zeta chain, deficiency (1) | 1q23-q2521.1 |
| Central core disease (3) | 14q12 |

-continued

| Disorder | Location |
|---|---|
| Central core disease of muscle (2) | 19q13.1 |
| Centrocytic lymphoma (2) | 11q13 |
| Cerebral amyloid angiopathy (1) | 20p11 |
| Cerebral arteriopathy with subcortical infarets and leukoencephalopathy (2) | 19q12 |
| Cerebrotendinous xanthomatosis (2) | 2q33-qter |
| Ceroid lipofuscinosis, neuronal-1, infantile (2) | 1p32 |
| Cervical carcinoma (2) | 11q13 |
| [CETP deficiency] (1) | 16q21 |
| Charcot-Marie-Tooth neuropathy, slow nerve conduction type Ia (2) | 17p11.2 |
| Charcot-Marie-Tooth neuropathy, slow nerve conduction type Ib (2) | 1q21.2-q23 |
| Charcot-Marie-Tooth neuropathy, X-linked-1, dominant (2) | Xq13 |
| Charcot-Marie-Tooth neuropathy, X-linked-2, recessive (2) | Xp22.2 |
| Cholesteryl ester storage disease (1) | 10q24-q25 |
| ?Chondrodysplasia punctata, rhisomellic (2) | 4p16-p14 |
| Chrondrodysplasia punctata, X-linked dominant (2) | Xq28 |
| Chrondrodysplasia punctata, X-linked recessive (2) | Xp22.3 |
| Choroideremia (2) | Xq21.2 |
| Chronic granulomatose disease, autosomal, due to deficiency of CYBA (3) | 16q24 |
| Chronic granulomatous disease due to deficiency of MCF-1 (1) | 7q11.23 |
| Chronic granulomatous disease due to deficiency of NCF-2 (1) | 1q25 |
| Chronic granulomatous disease, X-linked (3) | Xp21.1 |
| [Chronic infection, due to opsanin defect] (1) | 10q11.2-q21 |
| Citrullinemia (1) | 9q34 |
| Cleft palate, X-linked (2) | Xq13-q21.31 |
| ?Cleidocranial dysplasia (2) | 8q22 |
| CMO II deficiency (1) | 8q21 |
| Cockeye syndrome-2, late onset, 215410 (2) | 10q11 |
| Coffin-Lowry syndrome (2) | Xp22.2-p22.1 |
| Colon cancer, familial, nonpolyposis type 1 (2) | 2p16-p15 |
| Colorblindness, blue monochromatic (3) | Xq28 |
| Colorblindness, deutan (3) | Xq28 |
| Colorblindness, protan (3) | Xq28 |
| Colorblindness, tritan (2) | 7q22-qter |
| Colorectal adenoma (1) | 12p12.1 |
| Colorectal cancer (1) | 12p12.1 |
| Colorectal cancer (1) | 18q23.3 |
| Colorectal cancer (1) | 5q21 |
| Colorectal cancer, 114500 (3) | 17p13.1 |
| Colorectal cancer (3) | 5q21-q22 |
| Combined C5/C7 deficiency (1) | 5p13 |
| ?Combined variable hypogammaglobulinemia (1) | 14q32.33 |
| Congenital bilaterial absence of vas deference (1) | 7q81.2 |
| ?Conotruncal cardiac anomellen (2) | 22q11 |
| Contractural arachnodactyly, congenital (3) | Chr.5 |
| Coproparphyria (1) | Chr.9 |
| ?Cornelia de Lange syndrome (2) | 3q25.3 |
| [Coronary artery disease, susceptibility to] (1) | 6q27 |
| Cortisol resistance (1) | 5q31 |
| CR1 deficiency (1) | 1q32 |
| ?Craniofrontossal dysplasia (2) | Xpter-p22.2 |
| Craniosynostosis, type II (2) | 5q34-qter |
| Craniosynostosis, type I (2) | 7p21.3-21.2 |
| [Creatine kinase, brain type, extopic expression of] (2) | 14q32 |
| Creutzfeldt-Jakob disease, 123400 (3) | 20pter-p12 |
| Crigier-Najjar syndrome, type 1, 218800 (1) | Chr.2 |
| ?Cryptorchidism (2) | Xp21 |
| ?Cutis laxa, marfanoid neonatal type (1) | 7q31.1-31.3 |
| [Cystathioninuris] (1) | Chr.16 |
| Cystic fibrosis (3) | 7q31.2 |
| ?Cystimaria (2) | 14q32 |
| ?Cystimaria, 220100 (1) | 2pter-q32.3 |
| D | |
| Deafness, conductive with stapes fixation (2) | Xq13-q21.1 |
| Deafness, low tone (2) | 5q31-q33 |
| Debrisoquine sensitivity (1) | 22q13.1 |
| Dentinogenesis imperfecta-1 (2) | 4q13-q21 |
| Denys-Drash syndrome (1) | 11p13 |

-continued

| Disorder | Location |
|---|---|
| Diabetes insipidus, nephrogenic (3) | Xq28 |
| Diabetes insipidus, neurohypophyseal, 125700 (1) | 20p13 |
| ?Diabetes mellitus, insulin-dependent-1 (2) | 6p21.3 |
| Diabetes mellitus, insulin-resistant, with acanthosis nigricans (1) | 19p13.2 |
| Diabetes mellitus, rare form (1) | 11p15.5 |
| Diastrophic dysplasia (2) | 5q31-q34 |
| DiGeorge syndrome (2) | 22q11 |
| Diphenylhydantoin toxicity (1) | 1p11-qter |
| [Diphtheria, susceptibility to] (1) | 5q23 |
| DNA ligase 1 deficiency (1) | 19q15.2-q13.3 |
| ?Dubin-Johnson syndrome (2) | 13q34 |
| Duchenne muscular dystrophy (3) | Xp212 |
| [Dysalbuminemic hyperthyroxinemia] (1) | 4q11-q13 |
| [Dysalbuminemic hyperzincemia] (1) | 4q11-q13 |
| Dysantonomia, familial (2) | 9q31-q33 |
| Dysfibrinogenemia, alpha types (1) | 4q28 |
| Dysfibrinogenemia, beta types (1) | 4q28 |
| Dysfibrinogenemia, gamma types (1) | 4q28 |
| Dyskeratosis congenita (2) | Xq28 |
| ?Dyslexia-1 (2) | 15q11 |
| Dysplaminogenemic thrombophilia (1) | 6q26-q27 |
| Dysprothrombinemia (1) | 11p11-q12 |
| [Dystransthyretinemic hyperthyroxinemia] (1) | 18q11.2-q12.1 |
| E | |
| ?EEC syndrome (2) | 7q11.2-q21.3 |
| Ehlers-Danlos syndrome, type IV, 130050 (3) | 2q31 |
| Ehlers-Danlos syndrome, type VI, 225400 (1) | 1p36.3-p36.2 |
| Ehlers-Danlos syndrome, type VIIA1, 130060 (3) | 17q21.31-q22.05 |
| Ehlers-Danlos syndrome, type VIIA2, 130060 (3) | 7q22.1 |
| ?Ehlers-Danlos syndrome, type X (1) | 2p34 |
| [Elliptocytosis, Malaysian-Melanesian type] (1) | 17q21-q22 |
| Elliptocytosis-1 (3) | 1p36.2-p34 |
| Elliptocytosis-2 (2) | 1q21 |
| Elliptocytosis-3 (2) | 14q22-q23.2 |
| Emery-Dreifuss muscular dystrophy (2) | Xq28 |
| Emphysema (1) | 14q32.1 |
| Emphysema due to alpha-2-macroglobuline deficiency (1) | 12p13.3-p12.3 |
| Emphysema-cirrosis (1) | 14q32.1 |
| Endocaridal fibrolastosis-2 (2) | Xq28 |
| Enolase deficiency (1) | 1pter-p36.13 |
| ?Ensinophilic myeloprolliferative disorder (2) | 12p13 |
| Epidermalysis bullosa dystrophica, dominant, 131750 (3) | 3p21.3 |
| Epidermalysis bullosa dystrophica, recessive, 226600 (3) | 3p21.3 |
| Epidermalysis bullosa, Ogna type (2) | 8q24 |
| Epidermalysis bullosa simplex, 131900 (3) | 17q12-q21 |
| Epidermalysis bullosa simplex, Dowing-Meara type, 181760 (3) | 12q11-q13 |
| Epidermalysis bullosa simplex, Dowing-Meara type, 131760 (3) | 17q12-q21 |
| Epidermalysis bullosa simplex, generalized 131900 (1) | 12q11-q13 |
| ?Epidermalysis bullosa simplex, localized 131800 (1) | 12q11-q13 |
| ?Epidermalysis bullosa, Weber Cockayne type, 131800 (2) | 12q11-q13 |
| Epidermolytic hyperkeratosis, 118800 (1) | 17q21-q22 |
| Epidermolytic hyperkeratosis, 118800 (3) | 12q11-q13 |
| Epidermolytic palmophantar keratoderma (2) | 17q11-q23 |
| Epilepsy, genign neonatal (2) | 20q13.2-q13.3 |
| Epilepsy, juvenile myoclonic (3) | 6p21.3 |
| Epilepsy, progressive myoclonic (2) | 21q22.3 |
| Epithelioma, self-healing squamous 1, Ferguson-Smith type (2) | 9q31 |
| ?Erythremia (1) | 7q21 |
| Erythremias, alpha- (1) | 16pter-p13.3 |
| Erythremias, beta- (1) | 11p15.5 |
| Erythroblastosis fetalis (1) | 1p36.2-p34 |
| [Erythrocytosis, familial], 133100 (2) | 19p13.3-p13.2 |
| Erythrokeratodermia varibilis (2) | 1p36.2-p34 |
| [Euthyroidal hyper and hypothyrazinemia] (1) | Xq22 |
| Ewing sarcoma (3) | 22q12 |
| Exertional myoglobinuris due to deficiency of LDH-A (1) | 11p15.4 |
| Exadative vitreoretinopathy, X-linked (2) | Xq21.31 |

-continued

| Disorder | Location |
|---|---|
| F | |
| Fabry disease (3) | Xq22 |
| Facioscapulohumeral muscular dystrophy (3) | 4q35 |
| Factor H deficiency (1) | 1q32 |
| Factor V deficiency (1) | 1q23 |
| Factor VII deficiency (1) | 13q34 |
| Factor X deficiency (1) | 13q34 |
| Factor XI deficiency (1) | 4q35 |
| Factor XII deficiency (1) | 5q33-qter |
| Factor XIIIA deficiency (3) | 6p25-p24 |
| Factor XIIIB deficiency (1) | 1q31-q32.1 |
| Familial Mediterranean fever (2) | 16p13 |
| ?Fanconi anemia (1) | 1q42 |
| Fanconi anemia (2) | 20q13.2-q13.3 |
| Favism (1) | Xq23 |
| [?Fetal alcohol syndrome] (1) | 12q24.2 |
| ?Fetal hydantoin syndrome (1) | 1p11-qter |
| ?Fibrodysplasia ossificans progesssiva (1) | 20p12 |
| Fish-eye disease (3) | 16q22.1 |
| [Fish-odor syndrome] (1) | 1q |
| Fletcher factor deficiency (1) | 4q35 |
| Focal dermal hypoplasia (2) | Xp22.31 |
| Friedreich ataxia (2) | 9q13-q21.1 |
| Fructose intolerance (1) | 9q22 |
| Fucosidosis (1) | 1p34 |
| Fumarase deficiency (1) | 1q42.1 |
| G | |
| G6PD deficiency (3) | Xq26 |
| ?Galactokinase deficiency (1) | 17q21-q22 |
| Galactose epinerase deficiency (1) | 1p35-p35 |
| Galactosemia (1) | 9p13 |
| Galactosialidosis (1) | 20q13.1 |
| Gardner syndrome (3) | 5q21-q22 |
| Gaucher disease (1) | 1q21 |
| Gaucher disease, variant form (1) | 10q21-q22 |
| Genitourinary dyplasia (2) | 11p13 |
| Gerstmann-Straussler disease, 137440 (3) | 20pter-p12 |
| ?Gilbert syndrome, 143500 (1) | Chr2 |
| Glanzmann thrombasthenis, type A (1) | 17q21.32 |
| Glanzmann thrombasthenia, type B (1) | 17q21.32 |
| Glaucoma, congenital (2) | Chr.11 |
| Glaucoma, primary open angle (2) | 1q21-q31 |
| Glioblastoma multiforme (2) | 10p12-q23.2 |
| Glucose/galactose malasorption (1) | 22q11.2-qter |
| Glutaricacidemia type IIC (3) | 4q32-qter |
| Glutaricaciduna, type IIA (1) | 15q23-q25 |
| Glutaricaciduris, type IIB (2) | Chr.19 |
| Glutathioninuria (1) | 22q11.1-q11.2 |
| Glycerol kinase defciceny (2) | Xp21.3-p21.2 |
| Glycogen storage disease III (3) | 1p21 |
| Glycogen storage disease VII (1) | 1cen-q32 |
| Glycogen storage disease, X-linked hepatic (2) | Xp22.2-p22.1 |
| [Glyoxalase II deficiency] (1) | 16p13 |
| GM1-gangliosidosis (1) | 3p21-p14.2 |
| GM2-gangliosidosis, AB variant (1) | Chr.5 |
| GM2-gangliosidosis, juvenile adult (1) | 15q23-q24 |
| Goeminne TKCR syndrome (2) | Xq28 |
| Goiter, adolescent, multinodular (1) | 8q24.2-q24.3 |
| Goiter, nonendemic, simple (1) | 8q24.2-q24.3 |
| ?Goldenhar syndrome (2) | 7p |
| Gonadal dysgenesis, XY female type (2) | Xp22-p21 |
| Gonadal dysgenesis, XY type (1) | Yp11.3 |
| Gonadoblastoma (2) | 11p13 |
| ?Gonadotropin deficiency (2) | Xp21 |
| Greig craniopolysyndactyly syndrome (3) | 7p13 |
| ?Gynecomastia, familial, due to increased aromatase activity (1) | 15q21.1 |
| Gyrate atrophy of choroid and retina with ornithinemia, B6 responsive or unresponsive (1) | 10q26 |
| H | |
| Harderoporphyrinuria (1) | Chr.9 |
| ?Harthup disease, 234500 (1) | 2pter-q32.3 |
| Heinz body anemias, alpha- (1) | 16pter-p13.3 |
| Heinz body anemias, beta- (1) | 11p15.5 |

-continued

| Disorder | Location |
|---|---|
| Hemochromatosis (2) | 6p21.3 |
| Hemodialysis-related amyloidosis (1) | 15q21-q22 |
| Hemolytic anemia due to ADA excess (1) | 20q13.11 |
| Hemolytic anemias due to adenylate kinase deficiency (1) | 3q34.1 |
| Hemolytic anemias due to bisphosphoglycerate mutase deficiency (1) | 7q31-q34 |
| Hemolytic anemias due to G6PD deficiency (1) | Xq23 |
| Hemolytic anemias due to glucosphosphate isomerase deficiency (1) | 19q13.1 |
| Hemolytic anemias due to gluathione peroxidase deficiency (1) | 3q11-q12 |
| Hemolytic anemias due to glutathione reductase deficiency (1) | 8p21.1 |
| Hemolytic anemias due to hexokinase deficiency (1) | 10q22 |
| Hemolytic anemias due to PKG deficiency (1) | Xq13 |
| Hemolytic anemias due to phosphofructokinase deficiency (1) | 21q22.3 |
| Hemolytic anemias due to triosephosphate isomerase deficiency (1) | 12p13 |
| Hemophilia A (3) | Xq23 |
| Hemophilia B (3) | Xq27.1-q27.2 |
| Hemorrhagic diathesis due to "antithrombin" Pittsburgh (1) | 14q32.1 |
| Hemorrhagic diathesis due to PA11 deficiency (1) | 7q21.3-q22 |
| ?Hepatic lipase deficiency (1) | 15q21-q23 |
| ?Hepatocarcinoma (1) | 2q14-q21 |
| Hepatocellular carcinoma (3) | 4q32.1 |
| [Hereditary persistance of alpha-fetoprotein] (3) | 4q11-q13 |
| ?Hereditary persistance of fetal hemoglobin (3) | 11p15.5 |
| ?Hereditary persistance of fetal hemoglobin, heterocellular, indian type (2) | 7q36 |
| ?Hereditary persistence of fetal hemoglobin, Swiss type (2) | Xp11.23 |
| ?Hermansky-Padiak, syndrome, 203300 (1) | 15q15 |
| Hers disease, or glycogen storage disease VI (1) | Chr.14 |
| Heterocellular hereditary persistence of fetal hemoglobin (2) | 11p15 |
| [Hex A pseudodeficiency] (1) | 15q23-q24 |
| ?HHH syndrome (2) | 13q34 |
| [Histidinemia] (1) | 12q22-q23 |
| Holoprosencephaly, type 3 (2) | 7q36 |
| ?Holoprosencephaly-1 (2) | 18pter-q11 |
| ?Holoprosencephaly-2 (2) | 2p21 |
| ?Holoprosencephaly-4 (2) | 14q11.1-q13 |
| ?Holt-Oram syndrome (2) | 14q23-q24.2 |
| ?Holt-Oram syndrome (2) | 20p13 |
| Homocystinuria, B6-responsive and nonresponsive types (1) | 21q23.3 |
| HPFH, deletion type (1) | 11p15.5 |
| HPFH, nondeletion type A (1) | 11p15.5 |
| HPFH, nondeletion type G (1) | 11p15.5 |
| HPRT-related gout (1) | Xq26-q27.2 |
| ?Humoral hypercalcentria of malignancy (1) | 12p12.1-p11.2 |
| Huntington disease (2) | 4p16.3 |
| Hurler syndrome (1) | 4p16.3 |
| Hurler-Scheie syndrome (1) | 4p16.3 |
| Hydrocephalms due to aqueducts of Syivius, 307000 (3) | Xq23 |
| Hydrops fetalis, one form (1) | 19q13.1 |
| Hyperammonemia due to CTPase deficiency (1) | 1p13-p11 |
| Hyperbetalipoproteinemia (1) | 2p24 |
| Hypercalcemia, hypocalciaric, familial (2) | 3q21-q24 |
| Hypercholesteroliemia, familial (3) | 19p13.2-p13.1 |
| ?Hperglycinemia, isoloated nonketotic, type 1 (2) | 9p22 |
| ?Hyperimmunoglobulin G1 syndrome (2) | 14q32.33 |
| Hyperkalemic periodic paralysis (3) | 17q23.1-q25.3 |
| ?Hyperleucinemia-isoleucinemia or hypervalinemia (1) | 12pter-q12 |
| Hyperlipoproteinemia (1) | 8p22 |
| Hyperlipoproteinemia, type 1b (1) | 19q13.2 |
| Hyperlipoproteinemia, type III (1) | 19q13.2 |
| [Hyperphenylalanimemia, mild] (3) | 12q24:1 |
| [?Hyperproglucagonemia] (1) | 2q36-q37 |
| Hyperproinsulinemia, familial (1) | 11p15.5 |
| ?Hypertension, essential, 145500 (1) | 17q21-q22 |
| [Hypertension, essential, susceptibility to] (3) | 1q42-q43 |
| Hypertriglyceridimia, one form (1) | 11q23 |
| ?Hypervalinemia or hyperleucine-isoleucinemia (1) | Chr.19 |

-continued

| Disorder | Location |
|---|---|
| Hypoalphalipoproteinemia (1) | 11q23 |
| Hypobetalipoproteinemia (1) | 2p24 |
| Hypocaleturic hypercalcemia, type II (2) | 19p13.3 |
| [Hypoceruloplasminemia, hereditary] (1) | 3q21-q24 |
| Hypofibrinogenemia, gamma types (1) | 4q23 |
| ?Hypoglycemia due to PCK1 deficiency (1) | 20q13.31 |
| Hypogonadism, hypergonadoptropic (1) | 19q13.32 |
| ?Hypogonadism, hypogonadotropic due to GNRH deficiency, 227200 (1) | 8p21-p11.2 |
| Hypomangesemia, X-linked primary (2) | Xp22 |
| ?Hypomelanosis of lto (2) | 15q11-q13 |
| ?Hypomelanosis of lto (2) | 9q33-qter |
| Hypoparathyrodism, familial (1) | 11p15.3-p15.1 |
| Hypoparathyrodism, X-linked (2) | Xq26-q27 |
| ?Hypophosphatasia, adult, 148300 (1) | 1p36.1-p34 |
| Hypophosphatasia, infantile, 241500 (3) | 1p36.1-p34 |
| Hypophosphatemia, hereditary (2) | Xp22.2-p22.1 |
| ?Hypophosphatemia with deafness (2) | Xp22 |
| Hypoprothrombinemia (1) | 11p11-q12 |
| ?Hypospadias-dysphagia syndrome (2) | 5p13-p12 |
| Hypothyroidism, hereditary congenital (1) | 8q24.2-q24.3 |
| Hypothyroidism, nongoitrous (1) | 1p13 |
| Hypothyroidism, nongoitrous, due to TSH resistance (1) | 14q31 |
| I | |
| ?Ichthyosis vulgaris, 146700 (1) | 1q21 |
| Ichthyosis, X-linked (3) | Xp22.32 |
| ?Immotile cillia syndrome (2) | 6p |
| Immunodeficiency, X-linked, with hyper-IgM (3) | Xp24-q27 |
| Incontinentia pigmenti, familial (2) | Xp27-q28 |
| Incontinentia pigmenti, sporadic type (2) | Xp11.21 |
| Infertile male syndrome (1) | Xcen-q22 |
| [Inosien triphosphatase deficiency] (1) | 20p |
| Insomnia, fatal familial (3) | 20pter-p12 |
| ?Insulin-dependent diabetes melltus-2 (2) | 11q |
| Interferon, alpha, deficiency (1) | 9p21 |
| Interferon, immune, deficiency (1) | 12q24.1 |
| ?Isolated growth hormone deficiency due to defect in GHRF (1) | 20p11.23-qter |
| Isolated growth hormone deficiency, IIIig type with absent GH and Kowarski type with bioinactive GH (3) | 17q22-q24 |
| Isovalericacidemia (1) | 15q14-q15 |
| J | |
| ?Jacobsen syndrome (2) | 11q |
| K | |
| Kallmann syndrome (2) | Xp22.3 |
| [Kappa light chain deficiency] (1) | 2p12 |
| Keratoxis follicularis spinulosa decalvans (2) | Xp22.2-p21.2 |
| [Kiniogen deficiency] (1) | 3q26-qter |
| ?Kippel-Feli syndrome (2) | 5q11.2 |
| Kniest, dysplasia (1) | 12q13.11-q13.2 |
| ?Kostmann agranulocytosis (2) | 6p21.3 |
| Krabbe disease (1) | 14q24.3-q22.1 |
| L | |
| ?Lactase deficiency, adult 223100 (1) | Chr.2 |
| ?Lactase deficiency, congenital (1) | Chr.2 |
| ?Lactoferrin-deficient neutrophilis, 245480 (1) | 3q21-q23 |
| Langer-Giedion syndrome (2) | 8q24.11-24.13 |
| Langer-Saldino achondrogenesis-hypochrondrogenesis (1) | 12q13.11-q13.2 |
| Laron dwarfism (1) | 5p13-p12 |
| ?Laryngeal adductor paralysis (2) | 6p21.3-p21.2 |
| [Lead poisoning, susceptibility to] (1) | 9q34 |
| ?Leiomyomata, multiple hereditary cutaneous (2) | 18p11.32 |
| Leiomomatosis-nephropathy syndrome, 308940 (1) | Xq22 |
| Leprechanism (1) | 19p13.2 |
| Lesch-Nylan syndrome (3) | Xq26-q27.2 |
| ?Letterer-Siwe disease (2) | 13q14-q31 |
| Leukemia, acute lymphoblastic (1) | 19p13.3 |
| Leukemia, acute lymphoblastic (2) | 9p22-p21 |
| ?Leukemia, acute lymphocytic, with 4/11 translocation (3) | 4q21 |
| Leukemia, acute myeloid (3) | 21q22.3 |
| Leukemia, acute myeloid, M2 type (1) | Xp22.32 |

-continued

| Disorder | Location |
|---|---|
| Leukemia, acute pre-B-cell (2) | 1q23 |
| Leukemia, acute promyelocytic (1) | 17q21.1 |
| Leukemia, acute promyelocytic (2) | 15q22 |
| Leukemia, acute T-cell (2) | 11p13 |
| Leukemia, chronic myeloid (3) | 22q11.21 |
| Leukemia, chronic myeloid (3) | 9q34.1 |
| Leukemia, multilineage (2) | Chr.4 |
| Leukemia, myeloid/lymphoid of mixed-lineage (2) | 11q23 |
| Leukemia, T-cell acute lymphoblastic (2) | 11p15 |
| Leukemia, T-cell acute lymphoblastic (2) | 9q34.3 |
| Leukemia, T-cell acute lymphoblastoid (2) | 19p13.2-p13.1 |
| Leukemia, T-cell acute lymphocytic (2) | 10q24 |
| ?Leukemia, transient (2) | 21q11.2 |
| Leukemia-1, T-cell acute lymphoblastic (3) | 1p32 |
| Leukemia-1, T-cell acute lymphoblastic (3) | 9q31 |
| Leukemia/lymphoma, B-cell, 1 (2) | 11q13.3 |
| Leukemia/lymphoma, B-cell, 2 (2) | 18q21.3 |
| Leukemia/lymphoma, B-cell, 3 (2) | 19q13 |
| Leukemia/lymphoma, T-cell (2) | 14q32.1 |
| Leukemia/lymphoma, T-cell (2) | 2q34 |
| Leukemia/lymphoma, T-cell (3) | 14q11.2 |
| Leukocyte adhesion deficiency (1) | 21q22.3 |
| Li-Fraumeni syndrome (1) | 17p13.1 |
| Lipoamide dehydrogenase deficiency (1) | 7q31-q32 |
| Lipoma (2) | 12q13-q14 |
| Liver cell carcinoma (1) | 11p14-p13 |
| Long QT syndrome (2) | 11p15.5 |
| Lowe syndrome (3) | Xq26.1 |
| Lupus erythematosus, systemic, 152700 (1) | 1q23 |
| Lymphoproliferative syndrome, X-linked (2) | Xq25 |
| Lynch cancer family syndrome II (2) | 18q11-q12 |
| ?Lysosomal acid phosphatase deficiency (1) | 11p12-p11 |
| M | |
| Macrocytic anemia of 5q-syndrome, refractory (2) | 5q12-q32 |
| Macrocrytic anemia refractory, of 5q-syndrome, 153550 (3) | 5q31.1 |
| Macular dystrophy (1) | 6p21.1-cen |
| Macular dystrophy, atypical vitelliform (2) | 8q24 |
| Macular dystrophy, North Carolina type (2) | 6q14-q16.2 |
| Macular dystrophy, vitelliform type (2) | 11q13 |
| ?Male infertility due to acrosin deficiency (2) | 22q13-qter |
| ?Male infertility, familial (1) | 11p13 |
| ?Male pseudohermaphroditism due to defective LH (1) | 19q13.32 |
| Malignant hyperthermia susceptibility-1, 145600 (3) | 19q13.1 |
| Malignant hyperthermia susceptibility-2, 145600 (2) | 17q11.2-q24 |
| Malignant melanoma, cutaneous (2) | 1p36 |
| ?Manic-depressive illness, X-linked (2) | Xq28 |
| Mannosidosis (1) | 19p13.2-q12 |
| Maple syrup urine disease, type 1 (3) | 19q13.1-q13.2 |
| Maple syrup urine disease, type 2 (3) | 1p31 |
| Maple syrup urine disease, type 3 (1) | 6p22-p21 |
| Marian syndrome, 154700 (3) | 15q21.1 |
| Maroteraux-Lamy syndrome, several forms (1) | 5q11-q13 |
| Martin-Bell syndrome (2) | Xq27.3 |
| MASA syndrome (2) | Xq28 |
| McArdle disease (1) | 11q13 |
| McCune-Albright polyostotic fibrous dysplasia, 174800 (1) | 20q13.2 |
| [McLeod phenotype] (2) | Xp21.2-21.1 |
| Medullary thyroid-carcinoma (2) | 10q11.2 |
| Megacolon (2) | 10q11.2 |
| Megalocornea, X-linked (2) | Xq21.3-q22 |
| Melanoma, cutaneous malignant (2) | 9p21 |
| Meningioma (2) | 22q12.3-qter |
| Meningioma (3) | 22q12.3-q13.1 |
| Menkes disease (2) | Xq12-q13 |
| Mental retardation of WAGR (2) | 11p13 |
| Mental retardation, Snyder-Robinson type (2) | Xp21 |
| ?Mental retardation, X-linked nonspecific, with aphasia (2) | Xp11 |
| Mental retardation, X-linked, syndromic-1, with dystonic movements, ataxia, and seizures (2) | xp22.2-p22.1 |
| Mental retardation, X-linked, syndromic-2, with dysmorphism and cerebral atrophy (2) | Xp11-q21 |
| Mental retardation, X-linked, syndromic-3, with spastic diplegia (2) | Xp11-q21.3 |

-continued

| Disorder | Location |
|---|---|
| Mental retardation, X-linked, syndromic-4, with congenital contractures and low fingertip arches (2) | Xq13-q22 |
| Mental retardation, X-linked, syndromic-5, with Dandy-Walker malformation, basal ganglia disease, and seizures (2) | Xq25-q27 |
| Mental retardation, X-linked, syndromic-6, with gynecomastia and obesity (2) | Xp21.1-q22 |
| Mental retardation, X-linked-1, non-dysmorphic (2) | Xp22 |
| ?Mental retardation, X-linked-2, non-dysmorphic (2) | Xq11-q12 |
| Mental retardation, X-linked-3 (2) | Xq28 |
| Mental retardation-skeletal dysplasia (2) | Xq28 |
| Metahcromatic leukodystrophy (1) | 22q13.31-qter |
| Metahcromatic leukodystrophy due to deficiency of SAF-1 (1) | 10q21-q22 |
| Methemoglobinemia due to cytochrome b5 deficiency (3) | Chr.18 |
| Methemoglobinemia due to enzymopathic (1) | 22q13.31-qter |
| Methemoglobinemias, alpha- (1) | 16pter-p13.3 |
| Methemoglobinemias, beta- (1) | 11p15.5 |
| Methylmalonicaciduria, mutase deficiency type (1) | 6p21 |
| Mevalonicaciduria (1) | Chr.12 |
| ?Microphthalmia with linear skin defects (2) | Xp22.2 |
| Miller-Dieker lissencephaly syndrome (2) | 17p13.3 |
| ?Mitochoedrial complex 1 deficiency, 252010 (1) | 11q13 |
| MODY, one form (3) | 11p15.5 |
| MODY, type I (2) | 20q13 |
| MODY, type II, 125851 (3) | 7p15-p13 |
| ?Moebius syndrome (2) | 13q12.2-q13 |
| ?Monocyte carboxyesterase deficiency (1) | 16q13-q22.1 |
| Murolipidosis II (1) | 4q21-q23 |
| Murolipidosis III (1) | 4q21-q23 |
| Mucopolysaccaridosis I (1) | 4p16.3 |
| Mucopolysaccaridosis II (2) | Xq28 |
| Mucopolysaccaridosis IVA (3) | 16q24.3 |
| Mucopolysaccaridosis IVB (1) | 3p21-p14.2 |
| Mucopolysaccaridosis VII (1) | 7q21.11 |
| Multiple endocrine neoplasia I (1) | 11q13 |
| Multiple endocrine neoplasia II (2) | 10q11.2 |
| Multiple endocrine neoplasia III (2) | 10q11.5 |
| ?Multiple exostoses (2) | 8q22-q24.1 |
| ?Multiple lipomatosis (2) | 12q13-q14 |
| [Multiple scherosis, susceptibility to] (2) | 18q23-qter |
| ?Muscle glycogenosis (1) | Xq12-q13 |
| Muscular dystrophy, Duchenne-like, autosomal (2) | 13q12-q13 |
| Muscular dystrophy, limb-girdle, autosomal dominani (2) | 5q22.3-q31.3 |
| Muscular dystrophy, limb-girdle, autosomal recessive (2) | 15q15-q22 |
| Myelodysplastic syndrome, preleukemic (3) | 5q31.1 |
| Myelogenous leukemia, acute (3) | 5q31.1 |
| Myeloperoxidase deficiency (1) | 17q21.3-q22 |
| Myoadenylate deaminase deficiency (1) | 1p21-p13 |
| [Myocardial infarction, susceptibility to] (3) | 17q23 |
| Myoglobinuria/hemolysis due to PGK deficiency (1) | Xq13 |
| Myopathy due to CTPase deficiency (1) | 1p13-p11 |
| Myopathy due to phosphoglycerate mutase deficiency (1) | 7p13-p12.3 |
| Myopia-1 (2) | Xq28 |
| Myotonia congenita, atypical acetazolamide-responsive (2) | 17q23.1-q25.3 |
| Myotonia congenita, dominant, 160800 (2) | 7q35 |
| Myotonia congenita, recessive, 255700 (3) | 7q35 |
| Myotonic dystrophy (2) | 19q13.2-q13.3 |
| Myotubular myopathy, X-linked (2) | Xq28 |
| Myxoid liposarcoma (2) | 12q13-q14 |
| N | |
| ?N syndrome, 310465 (1) | Xp22.3-p21.1 |
| Nail-patella syndrome (2) | 9q34 |
| Nance-Horan syndrome (2) | Xp22.3-p21.1 |
| Nemaline myopathy-1 (2) | 1q21-q23 |
| Nephromonnthsis, juvenile (2) | 2p23-cen |
| Neuroblastoma (2) | 1p36.2-p36.1 |
| Neuroepithelioma, 133450 (1) | 11q23-q24 |
| Neuroepithelioma (2) | 22q12 |
| Neurofibromatosis, von Recklinghausen (3) | 17q11.2 |
| Neuropathy, recurrent, with pressure palsies, 162500 (3) | 17p11.2 |

-continued

| Disorder | Location |
|---|---|
| Neutropenia, immune (2) | 1q23 |
| Niemann-Pick disease, type A (1) | 11p15.4-15.1 |
| Niemann-Pick disease, type B (1) | 11p15.4-15.1 |
| Niemann-Pick disease, type C (2) | 18p |
| Nightblindness, congenital stationary, type 1 (2) | Xp11.3 |
| [Non-insulin dependent diabetes aneltins, susceptibility to] (2) | 19q13.3 |
| Norrie disease (2) | Xp11.4 |
| Norum disease (3) | 16q22.1 |
| Nucleoside phosphorylase deficiency, immunodeficiency due to (1) | 14q13.1 |
| O | |
| ?Obesity (2) | 7q31 |
| ?Ocular albinism autosoma recessive (2) | 6q13-q15 |
| Ocular albinis, Forsius-Erikson type (2) | Xp11-q11 |
| Ocular albinism, Nettleship-Falls type (2) | Xp22.3 |
| Ornithine transcarbamylase deficiency (3) | Xp21.1 |
| Orofacial cleft (2) | 6pter-p23 |
| Oroticaciduria (1) | 3q13 |
| Osterarthrosis, precocious (3) | 12q13.11-q13.2 |
| Osteogenesis imperfecta, 4 clinical forms, 166200, 166210, 259420, 166220 (3) | 17q21.31-q22.05 |
| Osteogenesis imperfecta, 4 clinical forms, 166200, 166210, 259420, 166220 (3) | 7q22.1 |
| ?Osteopetrosis, 257900 (1) | 1p21-p13 |
| Osteoporosis, idiopathic, 166710 (3) | 17q21.31-q22.05 |
| Osteosarcoma, 259500 (2) | 13q14.1-q14.2 |
| Otopalatodigital syndrome, type I (2) | Xq28 |
| Ovarian carcinoma, 16700 (2) | 19q13.1-q13.2 |
| Ovarian carcinoma (2) | 9p24 |
| Ovarian failure, premature (2) | Xq26-q27 |
| Oxolosis (1) | 2q36-q37 |
| P | |
| ?Paget disease of bone (2) | 6p21.3 |
| ?Pallister-Hall syndrome (2) | 3p25.3 |
| Pancreatic lipase deficiency (1) | 10q26.1 |
| ?Panhypopituitarism (1) | 3q |
| ?Panhypopituitarism, X-linked (2) | Xq21.3-q22 |
| Paraganglioma (2) | 11q22.3-q23.2 |
| Paramyuatonia congenita, 168300 (3) | 17q23.1-q25.3 |
| Parathyroid adenomatosis 1 (2) | 11q13 |
| ?Parietal formula (2) | 11p12-p11.12 |
| [?Parkinsonism, susceptibility to] (1) | 22q13.1 |
| Paraxysmal nocturnal hemoglobinuria (1) | Xq22.1 |
| Pelizaeus-Merabacher disease (3) | Xq22 |
| Pelviareteric junction obstruction (2) | 6p |
| ?Pendered syndrome (2) | 8q24 |
| Periodintitis, juvenile (2) | 4q11-q13 |
| Persistent Mullerian duct syndrome (1) | 19p13.3-p13.2 |
| Phenylketonuria (3) | 12q24.1 |
| Phenylketonuria due to dihydropteridine reductase deficiency (1) | 4p15.31 |
| Pheochronocytoma (2) | 1p |
| Phosphoribosyl pyrophosphatase synthetase-related gout (1) | Xq22-q24 |
| ?Phospharylase kinase deficiency of liver and muscle, 261750 (2) | 16q12-q13.1 |
| Piebaldism (3) | 4q12 |
| Pituitary tumro, growth-hormone-secreting (1) | 20q13.2 |
| PK deficiency hemolytic anemia (10 | 1q21 |
| [Placental-lactogen deficiency] (1) | 17q22-q24 |
| Placental steroid sulfatase deficiency (3) | Xp22.32 |
| Plasmia inhibitor deficiency (1) | 17pter-p12 |
| Plasminogen activator deficiency (1) | 8p12 |
| Plasminogen deficiency, types I and II (1) | 6q26-q27 |
| Plasminogen Tochigi disease (1) | 6q26-q27 |
| Platelet alpha/delta storage pool deficiency (1) | 1q23-q25 |
| [Polio, susceptibility to] (2) | 19q13.2-q13.3 |
| Polycystic kidney disease (2) | 16p13.31-p13.12 |
| Polycystic ovarian disease (1) | 17q11-q12 |
| Polyposis coli, familial (3) | 5q21-q22 |
| Pompe disease (1) | 17q23 |
| Porphyria, acute hepatic (1) | 9q34 |

-continued

| Disorder | Location |
|---|---|
| Porphyria, acute intermittent (1) | 11q24.1-q24.2 |
| Porphyria, Chester type (2) | 11q |
| Porphyria, congenital erythropoietic (1) | 10q25.2-q26.3 |
| Porphyria cutanea tarde (1) | 1p34 |
| Porphyria, hepatoerythropoietic (1) | 1p34 |
| Porphyria, variegata (2) | 14q32 |
| Postanesthetic apnea (1) | 3q26.1-q26.2 |
| Prader-Willi syndrome (2) | 15q11 |
| [Pre-eclampsia, susceptibility to] (3) | 1q42-q43 |
| Progressive cone dystrophy (2) | Xp21.1-p11.3 |
| Prolidase deficiency (1) | 19cen-q13.11 |
| Properdia deficiency, X-linked (3) | Xp11.4-p11.23 |
| Propionicacidemia, type I or pccA type (1) | 13q32 |
| Propionicacidemia, type II or pccB type (1) | 3q21-q22 |
| Protein C deficiency (1) | 2q13-q14 |
| Protein C inhibitor deficiency (2) | 14q32.1 |
| Protein S deficiency (1) | 3p11.1-11.2 |
| Proioporphyria, erythropoietic (1) | 18pter-p11.21 |
| Pseudohermaphroditism, male, with gynecomastia (1) | 17q11-q12 |
| Pseusohypoaldosteronism (1) | 4q31.1 |
| Pseudohypoparathyroidism, type Ia (1) | 20q13.2 |
| Pseudovaginal pertneocrotal, hypopadias (1) | Chr.2 |
| Pseudo-vitamin D dependency rickets I (2) | 12q14 |
| Pseudo-Zellweger syndrome (1) | 3p23-p22 |
| ?Pyrodoxine dependency with seizures (1) | 2q31 |
| Pyropoikilocytosis (1) | 1q21 |
| Pyruvate carboxylase deficiency (1) | 11q |
| Pyruvate dehydrogenase deficiency (1) | Xp22.2-p22.1 |
| R | |
| ?Rabson-Mendenhall syndrome (1) | 19p13.2 |
| ?Ragweed sensitivity (2) | 6p21.3 |
| Reifenstein syndrome (1) | Xcen-q22 |
| Renal cell carcinoma (2) | 3p14.2 |
| [Renal glucosuria] (2) | 6p21.3 |
| Renal tubular acidosis-osteopetrosis syndrome (1) | 8q22 |
| ?Retinal cone dystrophy-1 (2) | 6q25-q26 |
| ?Retinal cone-red dystrophy (2) | 18q21-q22.2 |
| Retinis pigmentosa, autosomal dominant (1) | 11p13 |
| Retinitis pigmentosa, autosomal recessive (3) | 3q21-q24 |
| Retinitis pigmentosa, peripheria-related (3) | 6p21.1-cea |
| Retinitis pigmentosa-1 (2) | 8p11-q21 |
| Retinitis pigmentosa-2 (2) | Xp11.3 |
| Retinitis pigmentosa-3 (2) | Xp21.1 |
| Retinitis pigmentosa-1, autosomal dominant (3) | 3q21-q24 |
| Retinitis pigmentosa-5 (2) | 3q |
| ?Retinitis pigmentosa-6 (2) | Xp21.3-p21.2 |
| Retinitis pigmentosa-9 (2) | 7p15.1-p13 |
| Retinitis pigmentosa-10 (2) | 7q |
| Retinitis punctata albeceas (1) | 6p21.1-cen |
| Retinoblastoma (3) | 13q14.1-q14.2 |
| ?Retinol binding protein, deficiency of (1) | 10q23-q24 |
| Retinoschisis (2) | Xp22.3-p22.1 |
| ?Rett syndrome (2) | Xp |
| Rhabdomyosarcoma (2) | 11p15.5 |
| Rhabdomyosarcoma, alveolar (2) | 2q37 |
| Rhabdomyosarcoma, alveolar (3) | 2q35 |
| Ry-mull disease (1) | 3cen-q22 |
| ?Rh-null hemolytic anemia (1) | 1p36.2-p34 |
| Rickets, vitamin D-resistant (1) | 12q12-q14 |
| Rieger syndrome (2) | 4q25-q27 |
| Rod monochromacy (2) | Chr.14 |
| ?Rothmund-Thomas syndrome (2) | Chr.8 |
| Rubinstein-Taybi syndrome (2) | 16p13.3 |
| ?Russell-Silver syndrome (2) | 17q25 |
| S | |
| Sacthre-Chotxen syndrome (2) | 7p |
| Salivary gland pleomorphic adenoma (2) | 8q12 |
| Sandhoff disease (1) | 5q13 |
| ?Sanfilippo disease, type IIIC (2) | Chr.14 |
| Sanfilippo syndrome D (1) | 12q14 |
| Sarcoma, synovial (2) | Xp11.2 |
| Scheie syndrome (1) | 4p16.3 |
| ?Schizophrenia (2) | 5q11.2-q13.3 |
| Schizophrenia, chronic (3) | 21q21.3-q22.05 |
| [?Schizophrenia, susceptibility to] (2) | 3q13.3 |

-continued

| Disorder | Location |
|---|---|
| Sclerotylosis (2) | 4q28-q31 |
| Severe combined immunodeficiency, 202500 (1) | 10p15-p14 |
| Severe combined immunodeficiency due to ADA deficiency (1) | 20q13.11 |
| Severe combined immunodeficiency due to IL2 deficiency (1) | 4q26-q27 |
| Severe combined immunodeficiency, HLA class II-negative type (1) | 19p13.1 |
| Severe combined immunodeficiency, X-linked, 300400 (3) | Xq13 |
| Short stature (2) | Xpter-p22.32 |
| ?Sialidosis (2) | 6p21.3 |
| Sickle cell anemia (1) | 11p15.5 |
| ?Simpson-Galabi-Behmel syndrome (2) | Xcen-q21.3 |
| ?Situs inversus vircerum (2) | 14q32 |
| ?SLE (1) | 1q32 |
| Small-cell cancer of lung (2) | 3p23-p21 |
| ?Smith-Lemli-Opitz syndrome (2) | 7q34-qter |
| Smith-Magenis syndrome (2) | 17p11.2 |
| Spastic paraplegis, X-linked, uncomplicated (2) | Xq21-q22 |
| Sphereocytosis, hereditary (3) | 17q21-q22 |
| Spherocytosis, hereditary, Japanese type (1) | 15q15 |
| Spherocytosis, recessive (1) | 1q21 |
| Spherocytosis-1 (3) | 14q22-q23.2 |
| Spherocytosis-2 (3) | 8p11.2 |
| Spinal and bulbar muscular atrophy of Kennedy, 313200 (3) | Xcen-q22 |
| Spinal muscular atrophy II (2) | 5q12.2-q13.3 |
| Spinal muscular atrophy III (2) | 5q12.2-q13.3 |
| Spinocerebellar ataxia-I (2) | 6p21.3-p21.2 |
| Spinocerebellar atrophy II (2) | 12q24 |
| Split-hand/foot deformity, type 1 (2) | 7q21.2-q21.3 |
| Split-hand/foot deformity, type 2 (2) | Xq26 |
| Spondyiopiphyseal dysplasia congenita (3) | 12q13.11-q13.2 |
| Spondyiopiphyseal dysplasia tarda (2) | Xp22 |
| Startle disease (2) | 5q33-q35 |
| Sticker syndrome (3) | 12q13.11-q13.2 |
| Sucrose intolerance (1) | 3q25-q26 |
| Supravalvar aortic stenosis (3) | 7q11.2 |
| T | |
| Tay-Sachs disease (1) | 15q23-q24 |
| Testicular feminizaiton (1) | |
| Thalassemias, alpha- (1) | 16pter-p13.3 |
| ?Thalassemias, beta- (1) | 11p15.5 |
| Thrombocytopenia, X-linked (2) | Xp21-p11 |
| Thrombophilia due to elevated HRG (1) | 3p14-qter |
| Thrombophilia due to excessive plasminogen activator inhibitor (1) | 7q21.3-q22 |
| Thrombophilia due to heparin cofactor II deficiency (1) | 22q11 |
| Thyroid hormone resistance, 264300, 188570 (3) | 3p24.3 |
| Thyroid iodine peroxidase deficiency (1) | 2p13 |
| Thyroid papillary carcinoma (1) | 10q11-q12 |
| Thyrotropin-releaseing hormone deficiency (1) | Chr.3 |
| Torsion dystonia (2) | 9q32-q34 |
| Torsion dystonia-parkinsonism, Filipino type (2) | Xq12-q21.1 |
| ?Tourette syndrome (2) | 18q22.1 |
| Transcobalamin II deficiency (1) | 22q11.2-qter |
| [Transcortin deficiency] (1) | 14q32.1 |
| Treacher Collins mandibulofacia dysoslosis (2) | 5q32-q33.1 |
| Trichlorhinophalangeal syndrome, type I (2) | 8q24.12 |
| Trypsinogen deficiency (1) | 7q32-qter |
| [?Tuberculosis, susceptibility to] (2) | 2q |
| Tuberous sclerosis-1 (2) | 9q33-q34 |
| ?Tuberous sclerosis-2 (2) | 11q23 |
| ?Tuberous sclerosis-3 (2) | 12q23.3 |
| ?Tuberous sclerosis-4 (2) | 16p13 |
| Turner syndrome (1) | Xq13.1 |
| Tyrostinemia, type I (1) | 15q23-q25 |
| Tyrostinemia, type II (1) | 16q22.1-q22.3 |
| U | |
| Urate oxidase deficiency (1) | 1p22 |
| Urolithiasis, 2,8-dihydroxyadenine (1) | 16q24 |
| Usher syndrome, type 1A (2) | 14q32 |
| Usher syndrome, type 1B (2) | 11q13.5 |

-continued

| Disorder | Location |
|---|---|
| Usher syndrome, type 1C (2) | 11p |
| Usher syndrome, type 2 (2) | 1q32 |
| V | |
| van der Woude syndrome (2) | 1q32 |
| Velocardiofacial syndrome (2) | 22q11 |
| Vitreoretinopathy, exudative, familial (2) | 11q13-q23 |
| Vitreoretinopathy, neovascular inflammatory (2) | 11q13 |
| [Vivax malaria, susceptibility to] (1) | 1q21-q22 |
| von Hippel-Lindau syndrome (2) | 3p26-p25 |
| von Willebrand disease (1) | 12pter-p12 |
| Waardenburg syndrome, type I (3) | 2q35 |
| Waardenburg syndrome, type III, | 2q35 |
| Xcen-q22 | 48820 (3) |
| Waisman parkinsonism-mental retardation syndrome (2) | Xq28 |
| Watson syndrome, 193520 (3) | 17q11.2 |
| Werdnig-Hoffmann disease (2) | 5q12.2-q13.3 |
| Werner syndrome (2) | 8p12-p11 |
| [Wernicke-Korsakoff syndrome, susceptibility to] (1) | 3p14.3 |
| Wieacher-Wolff syndrome (2) | Xq13-q21 |
| ?Williams-Beuren syndrome (2) | 4q33-q35.1 |
| Wilms tumor (2) | 11p13 |
| Wilms tumor, type 2 (2) | 11p15.5 |
| Wilson disease (2) | 13q14-q21 |
| Wiskott-Aldrich syndrome (2) | Xp11.3-p11.2 |
| ?Wolf-Hirschhorn syndrome, 194190 (3) | 4p16.1 |
| Wolf-Hirschhorn syndrome (2) | 4p16.3 |
| Wolman disease (1) | 10q24-q25 |
| Wrinkly skin syndrome (2) | 2q32 |
| X | |
| ?Xeroderma pigmentosum (1) | 1q42 |
| Xeroderma pigmentosum, group B (3) | 2q21 |
| Xeroderma pigmentosum, complementation group C (2) | Chr.5 |
| Xeroderma pigmentosum, group D, 278730 (1) | 19q13.2-q13.3 |
| Xeroderma pigmentosum, type A (1) | 9q34.1 |
| ?Xeroderma pigmentosum, type F (2) | Chr.15 |
| Z | |
| Zellweger syndrome, type II (1) | 1p22-p21 |
| Zellweger syndrome-1 (2) | 7q11-23 |

(reprinted from Culver, K. W., "Gene Therapy", 1994, p. 93, Mary Ann Liebert, Inc., Publishers, New York, N.Y.).

Alternatively tolerogenic conjugates may be submitted in accordance with U.S. Pat. No. 5,358,710 to Sehon et al., incorporated herein by reference in its entirety. Thus the present invention can readily be adapted to any gene therapy protocol and is generally applicable to the administration of any therapeutic immunogenic material and not just the specific examples listed above.

Gene therapy according to the existing art may be applied to somatic cells or germ line cells by methods known such as gold electroporation, microinjection or jet injection, or other methods as set forth in Sambrook et al. "Molecular Cloning: A Laboratory Manual, Cold Spring Harbor Press (1989)" incorporated herein by reference in its entirety.

Thus the invention provides for a method for treating by gene therapy a mammal with a therapeutic amount of a biologically active antigenic material or its expression product. To retain the effectiveness of said antigenic material(s) from counteraction by an antibody(ies) produced against it(them); it is essential to suppress the capacity of the recipient of the gene to mount an antibody response(s) to said biologically active antigenic material(s). This method comprises:

(a) selecting a mammal which has not received prior exposure to said biologically active antigenic material (s);

(b) administering to said mammal in step (a) an immunosuppressive effective amount of a tolerogenic covalent conjugate of said biologically active antigenic material, or an immunogenic fragment thereof, covalently bound to monomethoxypolyethylene glycol of a molecular weight of about 4,500 to 10,000, wherein said poly(ethylene glycol) is monomethoxypolyethylene glycol and said method suppresses the formation of about 98% of antibodies against said antigenic genetic material or its product, the effective amount of said conjugate suppressing in said mammal the formation of immunoglobulin antibodies against the antigenic genetic material(s); and subsequently (c) administering to said mammal a therapeutically effective amount of said biologically active antigenic genetic material alone, or a derivative thereof synthesized by conjugating to said antigenic genetic material the DNA expressing biologically or pharmacologically active molecules, wherein said tolerogenic conjugate of step (b) is administered at least one day prior to said antigenic genetic material of step (c).

In an alternative embodiment, the invention provides a method for suppressing the capacity of a mammal to mount an IgG class antibody response to a biologically active antigenic product of genetic material comprising:

(a) selecting a mammal which has not received prior exposure to said biologically active antigenic genetic material;

(b) administering to said mammal of step (a), a tolerogenic covalent conjugate comprising said biologically active antigenic genetic material or an immunogenic fragment thereof, covalently bound to monomethoxypoly(ethylene glycol) of a molecular weight of about 4,500 to 10,000, in an immunosuppressive effective amount capable of suppressing the formation of immunoglobulin antibodies of the IgG immunoglobulin class against said antigenic genetic material; and subsequently (c) administering to said mammal a therapeutically effective amount of said biologically active antigenic genetic material alone or an immunogenic derivative of said genetic material, wherein said mammal is suppressed from mounting an IgG class antibody response to said biologically active antigenic genetic material or immunogenic derivative thereof, wherein said tolerogenic conjugate of step (b) is administered at least one day prior to said antigenic protein of step (c).

The purpose of the above description and examples is to illustrate some embodiments of the present invention without implying any limitation. It will be apparent to those of skill in the art that various modifications and variations may be made to the composition and method of the present invention without departing from the underlying principles or scope of the invention. All patents and publications cited herein are incorporated by reference in their entireties.

We claim:

1. In a method for gene therapy comprising administration of a gene therapy vector comprising a gene encoding an antigenic protein operably linked to a promoter, the improvement comprising the step of at least one day prior to administration of said gene therapy vector, administering to a mammal a tolerogenic conjugate consisting of a protein coupled to monomethoxypolyethylene glycol (mPEG) having a molecular weight of about 2,000–10,000 daltons, wherein said protein is identical to the antigenic protein encoded by said gene, and wherein said gene is expressed at a level sufficient for gene therapy as a result of the suppression of an immune response to the antigenic protein encoded by said gene.

2. In a method for gene therapy according to claim 1, wherein said gene therapy vector is selected from the group consisting of Moloney murine leukemia virus vector, adenovirus vector, and vaccinia virus vector.

3. In a method for gene therapy comprising administration of a DNA encoding an antigenic protein operably linked to a promoter, the improvement comprising the step of at least one day prior to administration of said DNA, administering to a mammal a tolerogenic conjugate consisting of a protein conjugated to monomethoxypolyethylene glycol (mPEG) having a molecular weight of about 2,000–10,000 daltons, wherein said protein is identical to the antigenic protein encoded by said DNA, and wherein said DNA is expressed at a level sufficient for gene therapy as a result of the suppression of an immune response to the antigenic protein encoded by said DNA.

* * * * *